United States Patent
Makower

(10) Patent No.: US 10,602,966 B2
(45) Date of Patent: Mar. 31, 2020

(54) SYSTEM AND METHOD FOR DETECTING CHARACTERISTICS OF EUSTACHIAN TUBE

(71) Applicant: Acclarent, Inc., Menlo Park, CA (US)

(72) Inventor: Joshua Makower, Los Altos, CA (US)

(73) Assignee: Acclarent, Inc., Irvine, CA (US)

( * ) Notice: Subject to any disclaimer, the term of this patent is extended or adjusted under 35 U.S.C. 154(b) by 850 days.

(21) Appl. No.: 14/827,568

(22) Filed: Aug. 17, 2015

(65) Prior Publication Data

US 2016/0287145 A1     Oct. 6, 2016

Related U.S. Application Data

(60) Provisional application No. 62/140,708, filed on Mar. 31, 2015.

(51) Int. Cl.
| | |
|---|---|
| *A61B 5/12* | (2006.01) |
| *A61M 16/06* | (2006.01) |
| *A61B 5/00* | (2006.01) |
| *A61M 16/10* | (2006.01) |
| *A61B 17/24* | (2006.01) |
| *A61M 13/00* | (2006.01) |
| *A61B 5/107* | (2006.01) |

(52) U.S. Cl.
CPC ............. *A61B 5/12* (2013.01); *A61B 5/4836* (2013.01); *A61B 5/6817* (2013.01); *A61B 5/7282* (2013.01); *A61B 17/24* (2013.01); *A61M 16/06* (2013.01); *A61M 16/10* (2013.01); *A61B 5/1075* (2013.01); *A61B 5/4884* (2013.01); *A61B 5/6803* (2013.01); *A61B 5/7246* (2013.01); *A61B 2562/0247* (2013.01); *A61M 13/003* (2013.01); *A61M 2210/0675* (2013.01)

(58) Field of Classification Search
CPC ................................ A61B 5/6817; A61B 5/12
See application file for complete search history.

(56) References Cited

U.S. PATENT DOCUMENTS

| | | | | |
|---|---|---|---|---|
| 4,546,779 A | * | 10/1985 | Meno | A61B 1/233 |
| | | | | 600/559 |
| 6,716,813 B2 | | 4/2004 | Lim et al. | |
| 8,714,153 B2 | * | 5/2014 | Scarberry | A61B 5/087 |
| | | | | 128/204.18 |

(Continued)

FOREIGN PATENT DOCUMENTS

FR     1567403     *     5/1969

OTHER PUBLICATIONS

St. Croix, et al., "Genes Expressed in Human Tumor Endothelium," Science, Aug. 18, 2000, vol. 289, pp. 1197-1201, 6 pgs.
U.S. Appl. No. 62/140,708, filed Mar. 31, 2015.

*Primary Examiner* — Daniel L Cerioni
*Assistant Examiner* — Yasmeen S Warsi
(74) *Attorney, Agent, or Firm* — Frost Brown Todd LLC

(57) ABSTRACT

A method for detecting characteristics of a Eustachian tube of a patient includes communicating pressurized air into an oro-nasal cavity of the patient. The method further includes directing an energy signal into the oro-nasal cavity. The method further includes detecting transmission of the energy signal from the oro-nasal cavity through the Eustachian tube with a sensor. The method further includes determining at least one characteristic of the Eustachian tube based on whether the energy signal is detected by the sensor.

20 Claims, 12 Drawing Sheets

(56) References Cited

U.S. PATENT DOCUMENTS

| | | |
|---|---|---|
| 2010/0030031 A1 | 2/2010 | Goldfarb et al. |
| 2010/0274188 A1 | 10/2010 | Chang et al. |
| 2013/0274715 A1 | 10/2013 | Chan et al. |
| 2015/0374963 A1 | 12/2015 | Chan et al. |

* cited by examiner

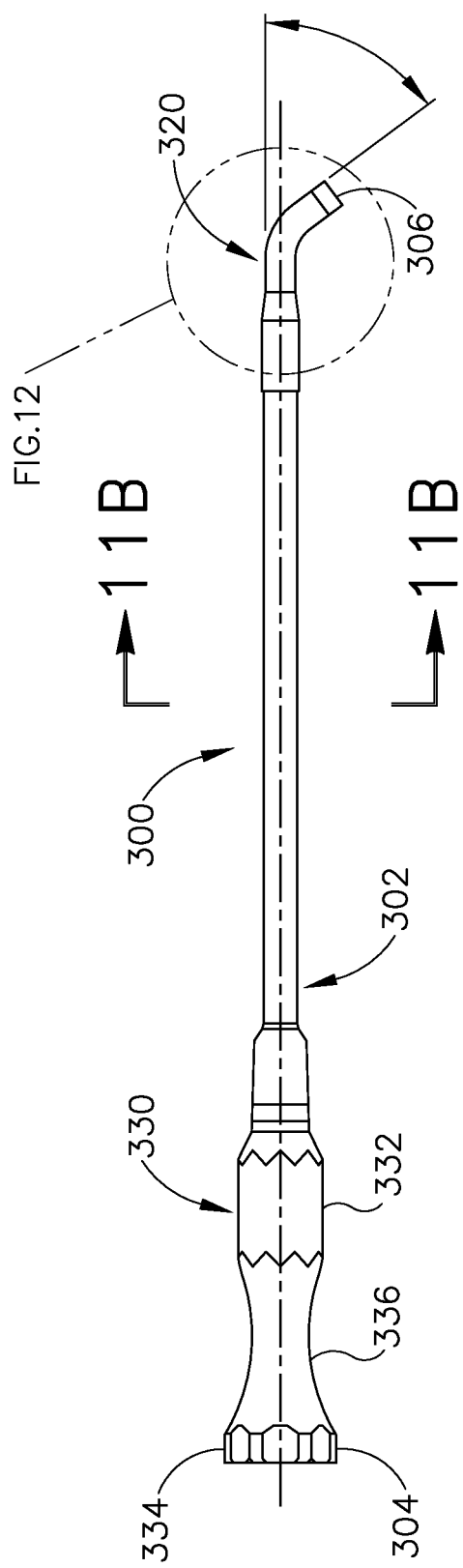
Fig.11A
Fig.11B
Fig.12

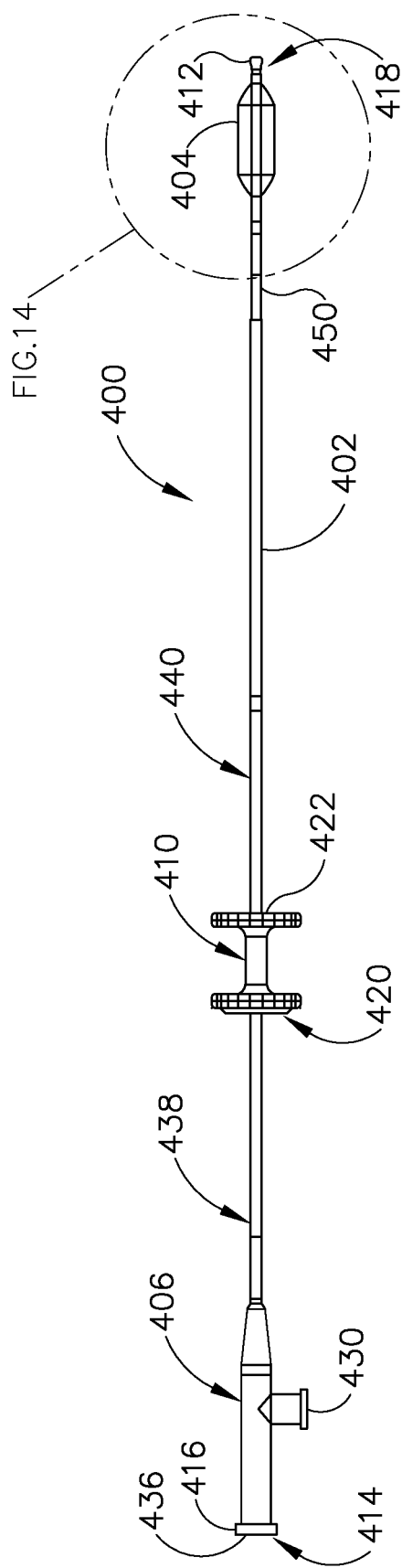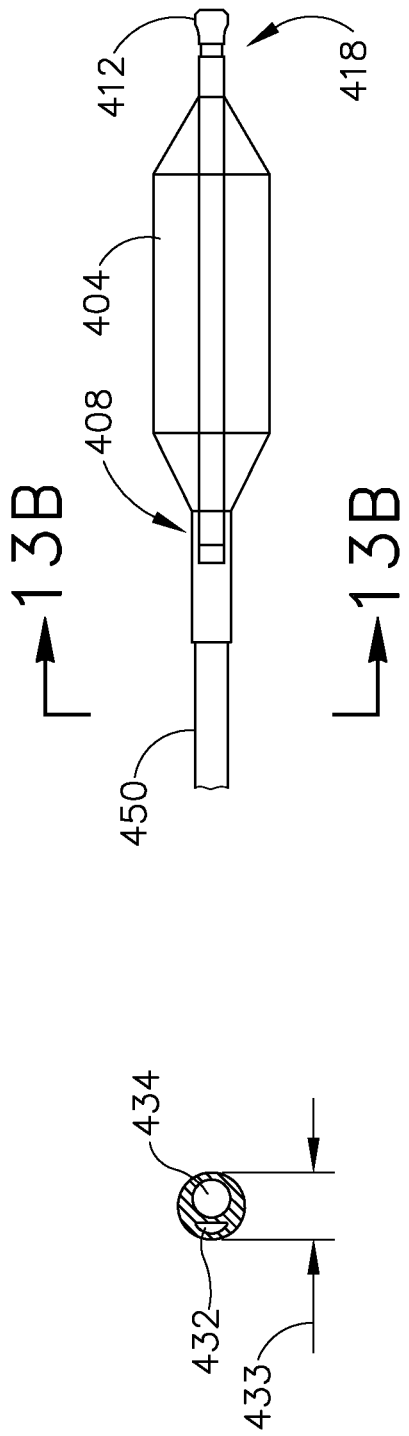
Fig. 13A
Fig. 13B
Fig. 14

SYSTEM AND METHOD FOR DETECTING CHARACTERISTICS OF EUSTACHIAN TUBE

PRIORITY

This application claims priority to U.S. Provisional Pat. App. No. 62/140,708, entitled "System and Method for Detecting Characteristics of Eustachian Tube," filed Mar. 31, 2015, the disclosure of which is incorporated by reference herein.

BACKGROUND

Referring to FIGS. 1-3, the ear (10) is divided into three parts: an external ear (12), a middle ear (14) and an inner ear (16). The external ear (12) consists of an auricle (18) and ear canal (20) that gather sound and direct it toward a tympanic membrane (22) (also referred to as the eardrum) located at an inner end (24) of the ear canal (20). The middle ear (14) lies between the external and inner ears (12, 16) and is connected to the back of the throat by a Eustachian tube (ET) (26), which serves as a pressure equalizing valve between the ear (10) and the sinuses. The ET (26) terminates in a pharyngeal ostium (28) in the nasopharynx region (30) of the throat (32). In addition to the eardrum (22), the middle ear (14) also consists of three small ear bones (ossicles): the malleus (34) (hammer), incus (36) (anvil) and stapes (38) (stirrup). These bones (34, 36, 38) transmit sound vibrations to the inner ear (16) and thereby act as a transformer, converting sound vibrations in the canal (20) of the external ear (12) into fluid waves in the inner ear (16). These fluid waves stimulate several nerve endings (40) that, in turn, transmit sound energy to the brain where it is interpreted.

The ET (26) is a narrow, one-and-a-half inch long channel connecting the middle ear (14) with the nasopharynx (30), the upper throat area just above the palate, in back of the nose. The ET (26) functions as a pressure equalizing valve for the middle ear (14), which is normally filled with air. When functioning properly, the ET (26) opens for a fraction of a second periodically (about once every three minutes) in response to swallowing or yawning. In so doing, it allows air into the middle ear (14) to replace air that has been absorbed by the middle ear lining (mucous membrane) or to equalize pressure changes occurring on altitude changes. Anything that interferes with this periodic opening and closing of the ET (26) may result in hearing impairment or other ear symptoms.

Obstruction or blockage of the ET (26) results in a negative middle ear pressure (14), with retraction (sucking in) of the eardrum (22). In adults, this is usually accompanied by some ear discomfort, a fullness or pressure feeling and may result in a mild hearing impairment and head noise (tinnitus). There may be no symptoms in children. If the obstruction is prolonged, fluid may be drawn from the mucous membrane of the middle ear (14), creating a condition referred to as serous otitis media (fluid in the middle ear). This occurs frequently in children in connection with an upper respiratory infection and accounts for the hearing impairment associated with this condition.

A lining membrane (mucous membrane) of the middle ear (14) and ET (26) is connected with, and is the same as, the membrane of the nose (42), sinuses (44) and throat (32). Infection of these areas results in mucous membrane swelling which in turn may result in obstruction of the ET (26). This is referred to as serous otitis media, which as discussed above is essentially a collection of fluid in the middle ear (14). Serous otitis media can be acute or chronic, and may be the result of blockage of the distal opening (28) of the ET (26), which leads to the accumulation of fluid in the middle ear (14). In the presence of bacteria, this fluid may become infected, leading to an acute suppurative otitis media (infected or abscessed middle ear). When infection does not develop, the fluid remains until the ET (26) again begins to function normally, at which time the fluid is absorbed or drains down the tube into the throat (32) through the pharyngeal ostium (28).

Chronic serous otitis media may result from longstanding ET blockage, or from thickening of the fluid so that it cannot be absorbed or drained down the ET (26). This chronic condition may lead to hearing impairment. There may be recurrent ear pain, especially when the individual catches a cold. Fortunately, serous otitis media may persist for many years without producing any permanent damage to the middle ear mechanism. The presence of fluid in the middle ear (14), however, makes it very susceptible to recurrent acute infections. These recurrent infections may result in middle ear damage.

When the ET (26) contains a build-up of fluid, a number of things may occur. First, the body may absorb the air from the middle ear (14), causing a vacuum to form that tends to pull the lining membrane and ear drum (22) inwardly, causing pain. Next, the body may replace the vacuum with more fluid, which tends to relieve the pain, but the patient can experience a fullness sensation in the ear (10). Treatment of this condition with antihistamines and decongestants can take many weeks to be fully effective. Finally, the fluid can become infected, which can lead to pain, illness, and temporary hearing loss. If the inner ear (14) is affected, the patient may feel a spinning or turning sensation (vertigo). The infection may be treated with antibiotics.

However, even if antihistamines, decongestants, and antibiotics are used to treat an infection or other cause of fluid build-up in the middle ear (14), these treatments may not immediately resolve the pain and discomfort caused by the buildup of fluid in the middle ear (14). The most immediate relief may be felt by the patient if the fluid can be removed from the ET (26).

Antibiotic treatment of middle ear infections may result in normal middle ear function within three to four weeks. During the healing period, the patient can experience varying degrees of ear pressure, popping, clicking and fluctuation of hearing, occasionally with shooting pain in the ear. Resolution of the infection may leaves the patient with uninfected fluid in the middle ear (14), localized in the ET (26).

Fluid build-up caused by these types of infections may be treated surgically. The primary objective of surgical treatment of chronic serous otitis media may be to reestablish ventilation of the middle ear, keeping the hearing at a normal level and preventing recurrent infection that might damage the eardrum membrane and middle ear bones. One method to opening the ET (26) includes the "Valsalva" maneuver, accomplished by forcibly blowing air into the middle ear (14) while holding the nose, often called popping the ear (see FIG. 3). This method may be effective for opening the ET (26) but it may not clear the accumulated fluid from the middle ear (14) and is essentially a temporary fix when fluid is present in the middle ear (14).

Methods for treating the middle ear (14) and ET (26) include those disclosed in U.S. Patent Pub. No. 2010/0274188, entitled "Method and System for Treating Target Tissue Within the Eustachian Tube," published on Oct. 28, 2010, now abandoned, the disclosure of which is incorporated by reference herein; U.S. Patent Pub. No. 2013/0274715, entitled "Method and System for Eustachian Tube Dilation," published as on Oct. 17, 2013, now abandoned, the disclosure of which is incorporated by reference herein; and U.S. patent application Ser. No. 14/317,269, entitled "Vent Cap for a Eustachian Tube Dilation System," filed Jun. 27, 2014, issued as U.S. Pat. No. 10,350,396 on Jul. 16, 2019, the disclosure of which is incorporated by reference herein.

While a variety of surgical instruments have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 11A depicts a side elevational view of an exemplary guide catheter that may be used to position the dilation catheter of FIG. 13A.

FIG. 11B depicts a cross-sectional view of the guide catheter shown in FIG. 11A, taken along line 11B-11B of FIG. 11A.

FIG. 12 depicts an enlarged view of the distal end of the guide catheter shown in FIG. 11A.

FIG. 13A depicts a side elevational view of an exemplary balloon dilation catheter that may be used with the guide catheter of FIG. 11A.

FIG. 13B depicts a cross-sectional view of the balloon dilation catheter shown in FIG. 13A, taken along line 13B-13B of FIG. 14.

FIG. 14 depicts an enlarged view of the distal end of the balloon dilation catheter shown in FIG. 13A.

Figure 1:
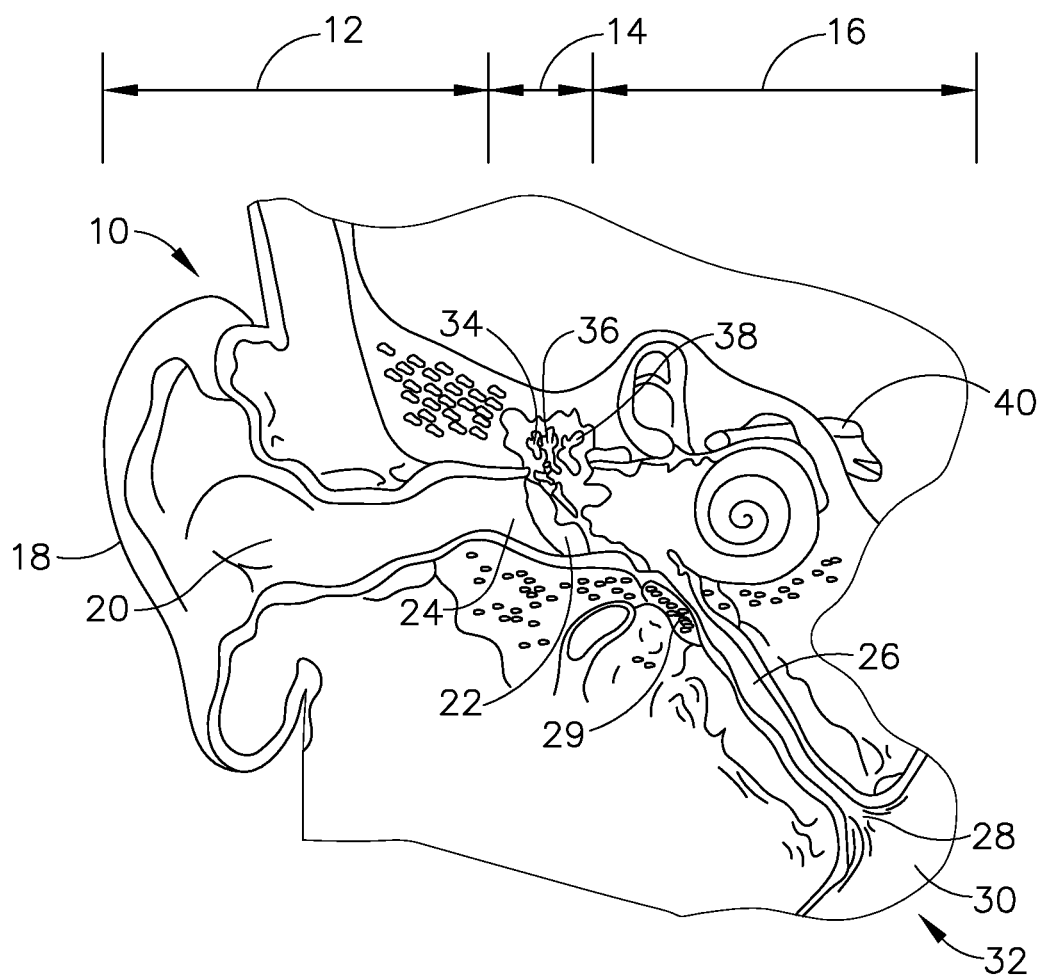
FIG. 1 depicts a cross-sectional view of a human ear showing the inner, middle and outer ear portions and the Eustachian tube connecting the middle ear with the nasopharynx region of the throat.
Figure 2:
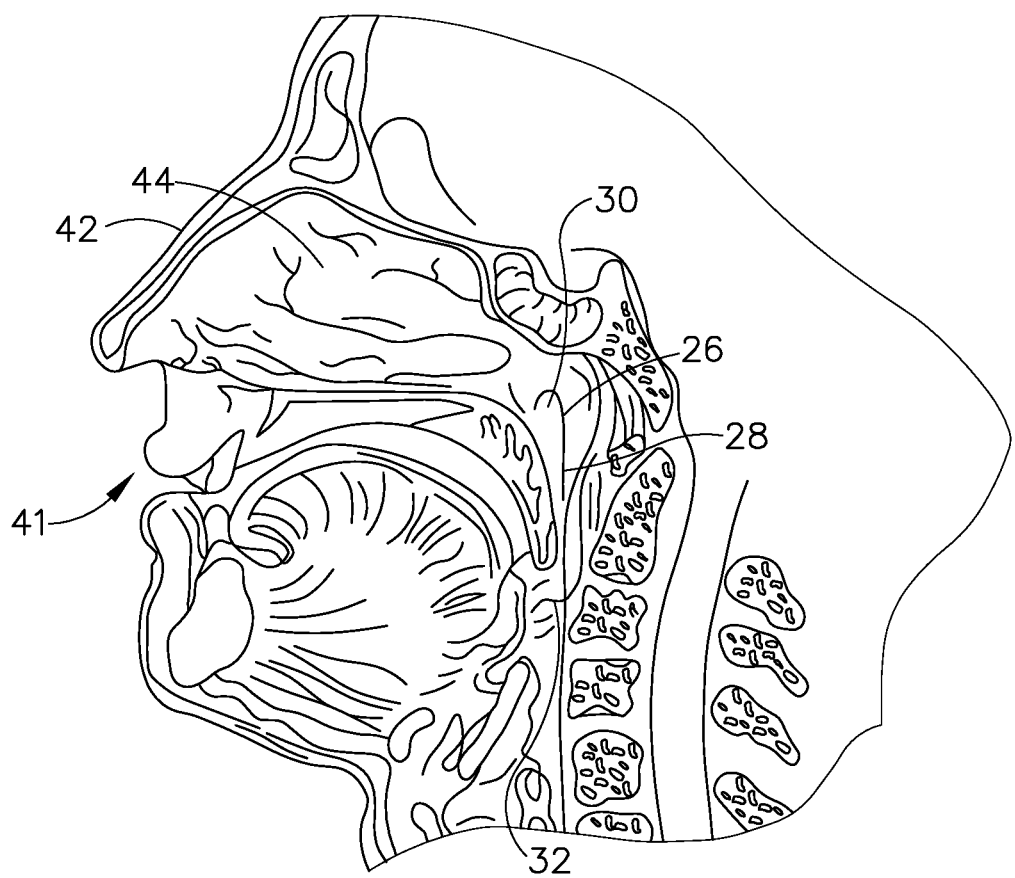
FIG. 2 depicts a cross-sectional view of a human head showing the nasopharynx region of the throat illustrated in FIG. 1 containing the pharyngeal ostium of the Eustachian tube illustrated in FIG. 1.
Figure 3:
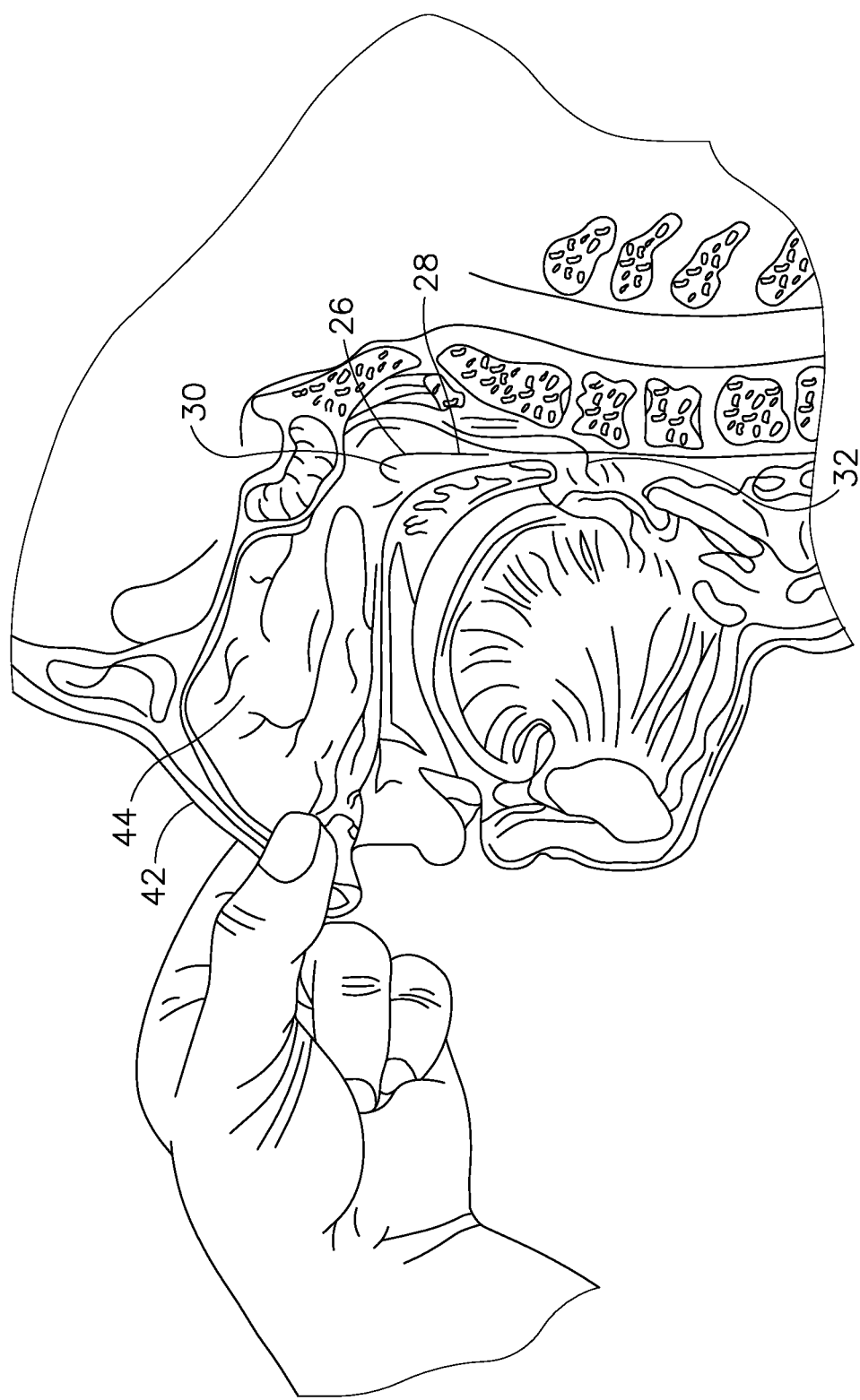
FIG. 3 depicts a cross-sectional view of a human head in the orientation shown in FIG. 2 showing the Valsalva maneuver for opening the Eustachian tube.

The drawings are not intended to be limiting in any way, and it is contemplated that various examples of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a surgeon or other operator grasping a surgical instrument having a distal surgical end effector. The term "proximal" refers the position of an element closer to the surgeon or other operator and the term "distal" refers to the position of an element closer to the surgical end effector of the surgical instrument and further away from the surgeon or other operator.

I. Exemplary System for Detecting Characteristics of ET

To determine the proper course of treatment of conditions associated with the ET (26), it is necessary to determine whether the ET (26) is normal or abnormal. Under normal functionality and typical pressure conditions (i.e., pressure conditions associated with breathing) of the oro-nasal cavity, a healthy and functional ET (26) should be closed. As the oro-nasal cavity pressure is increased, such as during the Valsalva maneuver discussed above, a normal ET (26) should open to relieve the pressure in the middle ear (14).

Thus, observing the state and behavior of the ET (26) at normal and changing pressure conditions within the oro-nasal cavity may provide an indication of the state of the ET (26).

Figure 4:
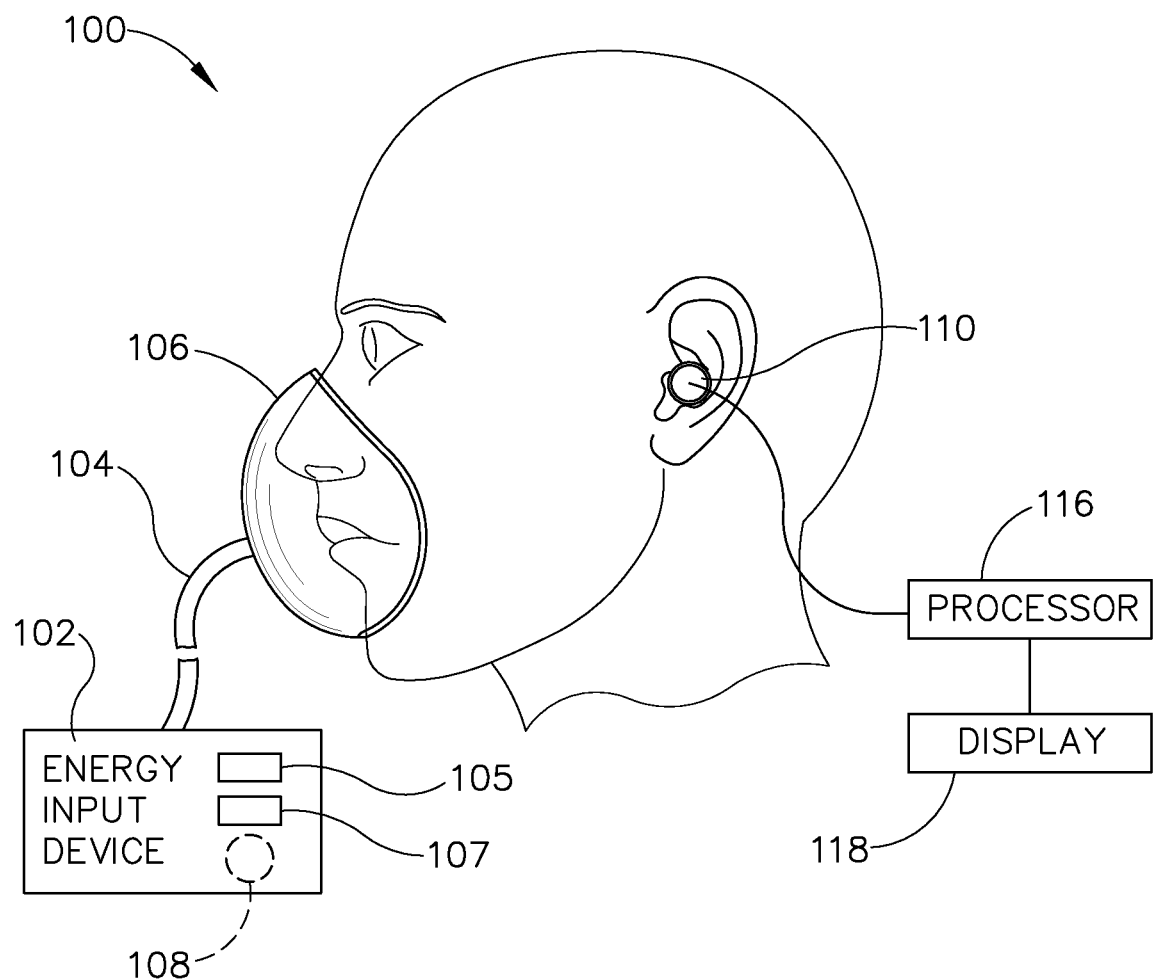
FIG. 4 depicts a schematic view of a system for detecting characteristics of Eustachian tube being used on a patient.

In the example shown in FIG. 4, a system (100) for detecting characteristics of ET (26) includes an energy input device (102) that is capable of communicating pressurized air into the oro-nasal cavity. The system (100) further includes a tube (104) extending from the energy input device (102) that couples the energy input device (102) with a facemask (106). Energy input device (102) is operable to selectively drive pressurized air through tube (104) to facemask (106). As shown, facemask (106) is configured to envelop a subject's nose (42) and mouth (41) such that the pressurized air may be directed into the oro-nasal cavity. Facemask (106), tube (104), and other system components may be configured to prevent the ingress or egress of light, sound, air, or other energy so as to prevent the interference of outside energy with the functioning of system (100), which will be further understood with reference to the disclosure below. By using energy input device (102) to direct pressurized air into the oro-nasal cavity and thereby increase the overall pressure of the oro-nasal cavity, the state of the ET (26) may be observed during changing pressure conditions. The pressurized air signal may be delivered by energy input device (102) at a constant or variable waveform, and may be simple or complex.

Energy input device (102) includes an air pump (105) and a valve assembly (107) that are together operable to deliver pressurized air to the subject via tube (104) and mask (106) without interfering with the subject's ability to breathe. Energy input device (102) further includes an energy emitter (108) that is configured to direct a second type of energy signal into the oro-nasal cavity. The second energy signal (also referred to herein as "second energy") may be at least one of sound waves, pressure waves, light, and/or other types of energy. By way of example only, energy emitter (108) may include a sound source, and facemask (106) may be configured to direct sound generated by the sound source into the patient's oro-nasal cavity. Alternatively, a speaker may be positioned on a feature that extends from facemask (106) into the patient's mouth, nose, or nasopharynx; and the speaker may be configured to direct sound generated by the sound source into the patient's oro-nasal cavity. As another merely illustrative example, energy emitter (108) may include a light source, and facemask (106) may be configured to direct light generated by the light source into the patient's oro-nasal cavity. Alternatively, a light emitter may be positioned on a feature that extends from facemask (106) into the patient's patient's mouth, nose, or nasopharynx; and the light emitter may be configured to direct light generated by the light source into the patient's oro-nasal cavity. Various suitable forms that energy emitter (108) and associated components may take will be apparent to those of ordinary skill in the art in view of the teachings herein.

The second energy signal may be delivered at a constant or variable waveform, and may be simple or complex. Moreover, the second energy signal may be a one-time signal (e.g., a "tone") or extended, and may be continuous or intermittent. The second energy may be emitted into the oro-nasal cavity at one portion of the oro-nasal cavity (e.g., on one side of the ET (26), such as the ear) and a sensor may be placed adjacent to or within another portion of the oro-nasal cavity (e.g., on another side of the ET (26), such as in the nasopharynx (30), mouth (41), nose (42), etc.). In the present example, the second energy may be such that it has limited ability to be transmitted through the ET (26) to the sensor unless the ET (26) is open. Thus, the sensor's detection of the second energy, or the lack thereof, may be indicative of the state of the ET (26). In one example, the quality, amplitude, and frequency of the second energy signal may be indicative of the open or closed state of the ET (26). For example, a low- or high-quality signal detection by sensor (110) may indicate the extent to which ET (26) may be open or closed.

Figure 5:
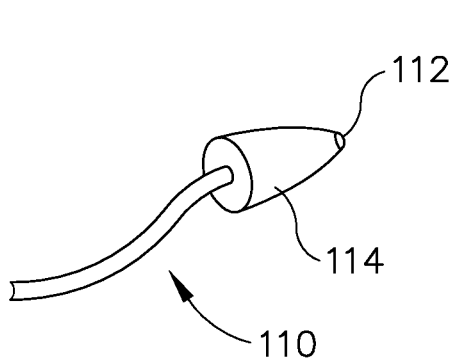
FIG. 5 depicts a perspective view of a sensor, provided on an earpiece, of the system of FIG. 4.
Figure 6:
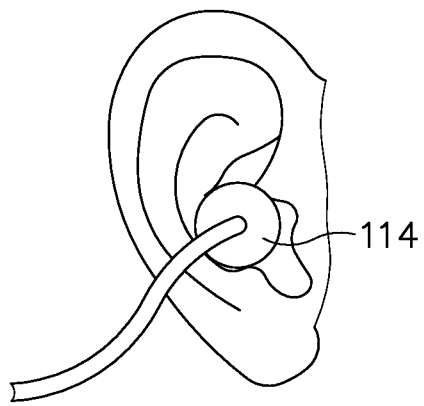
FIG. 6 depicts a side elevational view of the sensor of FIG. 4 inserted into a patient's ear.

Referring specifically to FIGS. 5-6, a sensor (110) of the present example comprises a sensing member (112) provided on an earpiece (114) that is insertable into the ear canal (20) of a patient. In the example shown, earpiece (114) comprises foam or a similar material in order to insulate sensing member (112) from outside noise interference, so as to prevent or reduce interference from undesired input signals (e.g., outside sound, light, pressure, etc). In other examples, the sensor (110) may be configured to be placed in other regions of the ear (10), including but not limited to other portions of the external ear (12), adjacent to the tympanic membrane (22), within the inner ear (16), or adjacent to the mastoid bone surrounding the ear (10). Sensing member (112) is configured to sense one or more types of energy signals, such as the second energy signals generated by energy emitter (108). As discussed above, the secondary energy signals may be at least one of sound waves (e.g., such that sensing member (112) may comprise a microphone), pressure waves (e.g., such that sensing member (112) may comprise a pressure sensor), light (e.g., such that sensing member (112) may comprise a photosensor), or other types of energy. Sensing member (112) is configured to communicate data to processor (116), with such data being indicative of the second energy signals sensed by sensing member (112).

In the present example, the second energy is emitted into the oro-nasal cavity at the nose (42)/mouth (41) via energy input device (102) and tube (104), and is sensed within or adjacent to the ear (10) by sensor (110). However, in other examples, the relative positions of energy emitter (108) and sensor (110) may be switched, such that energy emitter (108) may be positioned at or near an ear structure such that the second energy is emitted into the ear (10), while the sensor (110) may be configured to be placed elsewhere in the oro-nasal cavity (e.g., on the other side of the ET) in the nasopharynx (30), mouth (41), nose (42), etc.

In the example shown, system (100) also includes a processor (116) in communication with energy input device (102) and sensor (110). Processor (116) is configured to implement one or more algorithms to, for example, direct energy input device (102) to communicate pressurized air and emit one or more forms of energy into the oro-nasal cavity, to receive information regarding second energy signal(s) sensed by the sensor (110), to determine the state of the ET (26) based on that information, as discussed in more detail below, and/or to determine or recommend a course of treatment based on the state of the ET (26). Processor (116) and/or sensor (110) may be configured to filter out noise signals associated with, for example, natural sounds and other signals occurring within the head and body of the patient, as well as other signals and noises (e.g., sounds and light from outside the patient). System (100) of the present example also includes a display device (118) that may be configured to display settings of the energy input device (102) and readings of the sensor (110), for example. Display device (118) may also include a user interface to allow a user to control inputs of energy input device (102). In the example shown, energy input device (102), processor (116), and display (118) are all shown to be separate components.

However, in alternative examples, energy input device (102), processor (116), and/or display (118) may be integrated into one module or device. Moreover, energy emitter (108) may or may not be integral with energy input device (102). Various suitable components that may be incorporated into energy input device (102), sensor (110), processor (116), and display (118) will be apparent to those of ordinary skill in the art in view of the teachings herein. Similarly, various suitable ways in which the features of system (100) may be arranged will be apparent to those of ordinary skill in the art in view of the teachings herein.

II. Exemplary Methods for Determining Characteristics of ET

Figure 7:
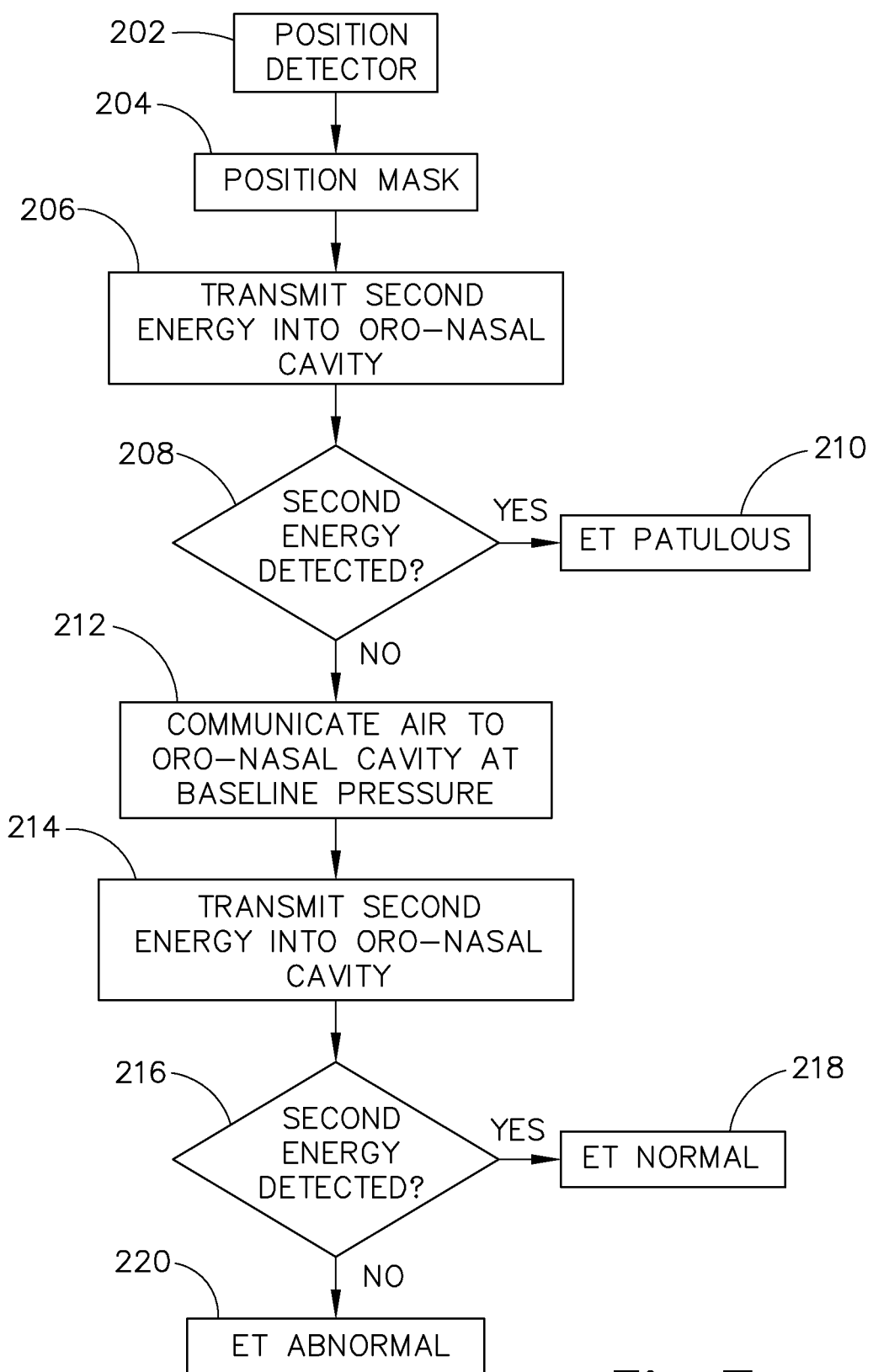
FIG. 7 depicts a flowchart detailing an exemplary method for detecting characteristics of Eustachian tube.
Figure 9:
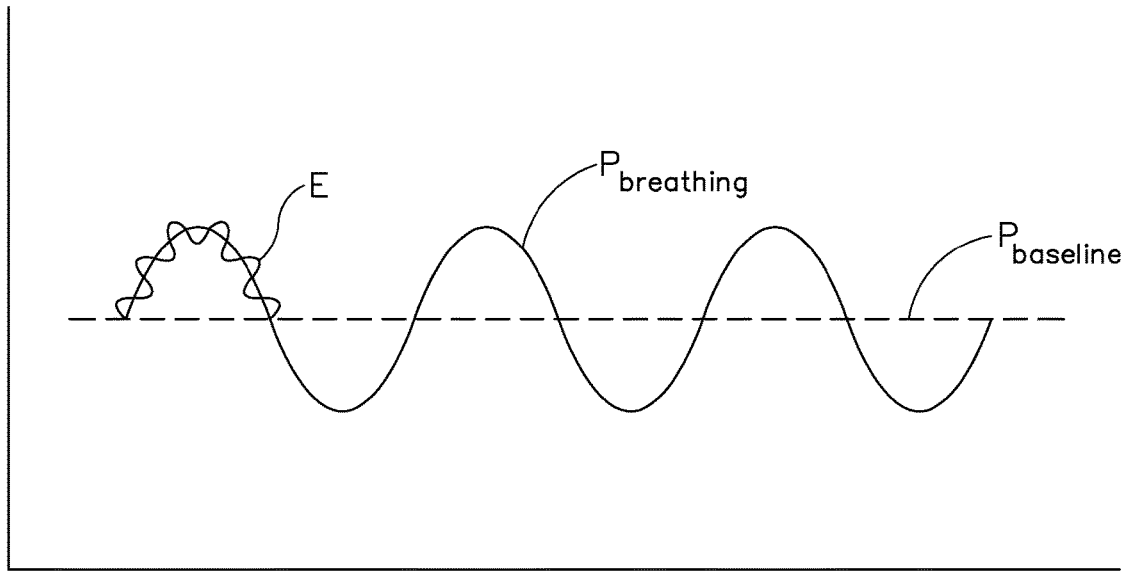
FIG. 9 depicts a graph detailing exemplary energy input data of the system of FIG. 4.

FIG. 7 is a flowchart of one exemplary method that is implementable using the system (100) of FIG. 4. In this example, after the sensor (110) and mask (106) are positioned on a subject (blocks 202 and 204), the second energy (e.g., second energy E, as shown in FIG. 9) is transmitted into the oro-nasal cavity (block 206). At this stage, the pressure in the oro-nasal cavity is unaltered, such that no pressurized air is being directed into the oro-nasal cavity. Processor (116) then evaluates if sensor (110) is detecting the second energy (block 208). If the second energy is detected by sensor (110), it is indicative of the ET (26) being in a patulous state (block 210). However, if the second energy is not detected by sensor (110), this is indicative of the ET (26) being in a closed state. System (100) will then communicate air to the oro-nasal cavity at a baseline pressure (block 212). In some instances, the operator may instruct the patient to stop breathing as air is being communicated to the oro-nasal cavity at the baseline pressure. As air is being communicated to the oro-nasal cavity at the baseline pressure, system (100) will transmit the second energy into the oro-nasal cavity (block 214).

FIG. 9 graphically shows pressurized air being directed into the oro-nasal cavity from the energy input device (102) at a baseline pressure ($P_{baseline}$) (block 212) while the second energy (E) is emitted by the energy input device (102) into the oro-nasal cavity (block 214). Again, the operator may instruct the patient to continue refraining from breathing as second energy (E) is emitted by the energy input device (102) into the oro-nasal cavity. In the example shown in FIG. 9, the second energy E is emitted as relatively short pulse or tone, but in other examples, the second energy (E) may be emitted for a longer period of time (e.g., as long as the pressurized air is directed into the oro-nasal cavity). Thus, the overall pressure level within the oro-nasal cavity equals the baseline pressure plus or minus the pressure associated with normal breathing. The processor (116), energy input device (102), mask (106) or another portion of system (100) may include a pressure sensing device for measuring the pressure associated with normal breathing of the patient so that the overall pressure level may be calculated.

While air is being communicated to the oro-nasal cavity at the baseline pressure (block 212) with the second energy being simultaneously transmitted to the oro-nasal cavity (block 214), processor (116) evaluates if sensor (110) is detecting the second energy (block 216). If sensor (110) senses the second energy (block 216) as air is being communicated into the oro-nasal cavity (block 212) and second energy is being transmitted into the oro-nasal cavity (block 214), this is indicative that the overall pressure level within the oro-nasal cavity is sufficient to open the ET (26) from a closed state, and the ET (26) is deemed normal (block 218). However, if sensor (110) does not sense the second energy, this is indicative that the overall pressure level (e.g., $P_{baseline}$+$P_{breathing}$) is insufficient to open the ET (26) from a closed state, and thus that the ET (26) is abnormal (block 220).

In some instances, as soon as it is determined that the ET (26) is abnormal (block 220), the operator may wish to proceed directly to some form of treatment. Various examples of treatment are described in greater detail below. Alternatively, the operator may wish to perform additional testing in order to select a particular treatment from an array of various available treatments. For instance, referring to FIG. 8, once the ET (26) is deemed abnormal it may be desirable to determine the extent of the abnormality to determine a course of treatment. Because the overall pressure (assuming the same $P_{baseline}$ level used in the method of FIG. 7) was insufficient to open the abnormal ET (26), the baseline pressure of pressurized air delivered to the oro-nasal cavity is increased (block 222) and the second energy is transmitted into the oro-nasal cavity (block 224). The operator may instruct the patient to stop breathing as air is being communicated to the oro-nasal cavity at the increased pressure with the second energy being simultaneously transmitted to the oro-nasal cavity. While air is being communicated to the oro-nasal cavity at the increased pressure (block 222) with the second energy being simultaneously transmitted to the oro-nasal cavity (block 224), processor (116) evaluates if sensor (110) is detecting the second energy (block 226). If the second energy is detected (block 226), the pressure to open the ET (26) (ETOP) is recorded (block 228) and a treatment is selected based on the ETOP (block 230).

The general state or functionality of the ET (26) correlates with the ETOP. For example, if the ETOP equals approximately zero, then the ET is likely patulous. If the ETOP equals a predetermined pressure amount, it is normal, such that it will open and close according to normal pressure conditions in the oro-nasal cavity as described herein. If the ETOP is greater than the predetermined pressure amount, the ET (26) is likely inflamed or subject to disease. In some versions, system (100) is operable to automatically suggest a treatment based on the ETOP (block 230). For instance, processor (106) may execute an algorithm comparing the ETOP against historical data correlating certain medical conditions and/or treatment methods with particular ETOP values. System (100) may convey the suggested treatment to the operator via display (118). Alternatively, system (100) may simply convey the ETOP value to the operator via display (118) (or in some other fashion), and the operator may simply use their own judgment to select a treatment based on the ETOP (block 230).

Referring back to FIG. 8, if the second energy is not detected (block 226), processor (116) determines if the air pressure is at a maximum level yet (block 232). The maximum pressure may be selected to prevent injury to the subject. A suitable value for the maximum pressure will be apparent to those of ordinary skill in the art in view of the teachings herein. If processor (116) determines that the air pressure has not yet reached the maximum level, the pressure of air directed to the oro-nasal cavity is again increased (block 222), and the second energy continues to be directed into the oro-nasal cavity (block 224). While air is being communicated to the oro-nasal cavity at the further increased pressure (block 222) with the second energy being simultaneously transmitted to the oro-nasal cavity (block 224), processor (116) evaluates again if sensor (110) is detecting the second energy (block 226). If the second energy is still not detected, system (100) will continue to reiterate the process of checking whether the air pressure has reached the maximum level (block 232), increase the pressure further (222) if the maximum is not yet reached, transmit the second energy to the oro-nasal cavity (224), and evaluate again if sensor (110) is detecting the second energy (block 226). If the second energy is eventually detected (block 226), the pressure to open the ET (26) (ETOP) is recorded (block 228) and a treatment is selected based on the ETOP (block 230) as noted above.

In some cases, when processor (106) is determining if the air pressure is at a maximum level yet (block 232), the air pressure may have in fact reached the maximum level. Once the air pressure reaches a maximum (block 232), system (100) stops testing (block 234). A treatment is then selected based on the testing being stopped due to the maximum air pressure being reached (block 236). Some versions of system (100) may be operable to automatically suggest a treatment based on the testing being stopped due to the maximum air pressure being reached (block 236). System (100) may convey the suggested treatment to the operator via display (118). Alternatively, system (100) may simply inform the operator via display (118) (or in some other fashion) that the maximum air pressure has been reached, and the operator may simply use their own judgment to select a treatment based on the maximum air pressure being reached (block 236).

Figure 8:
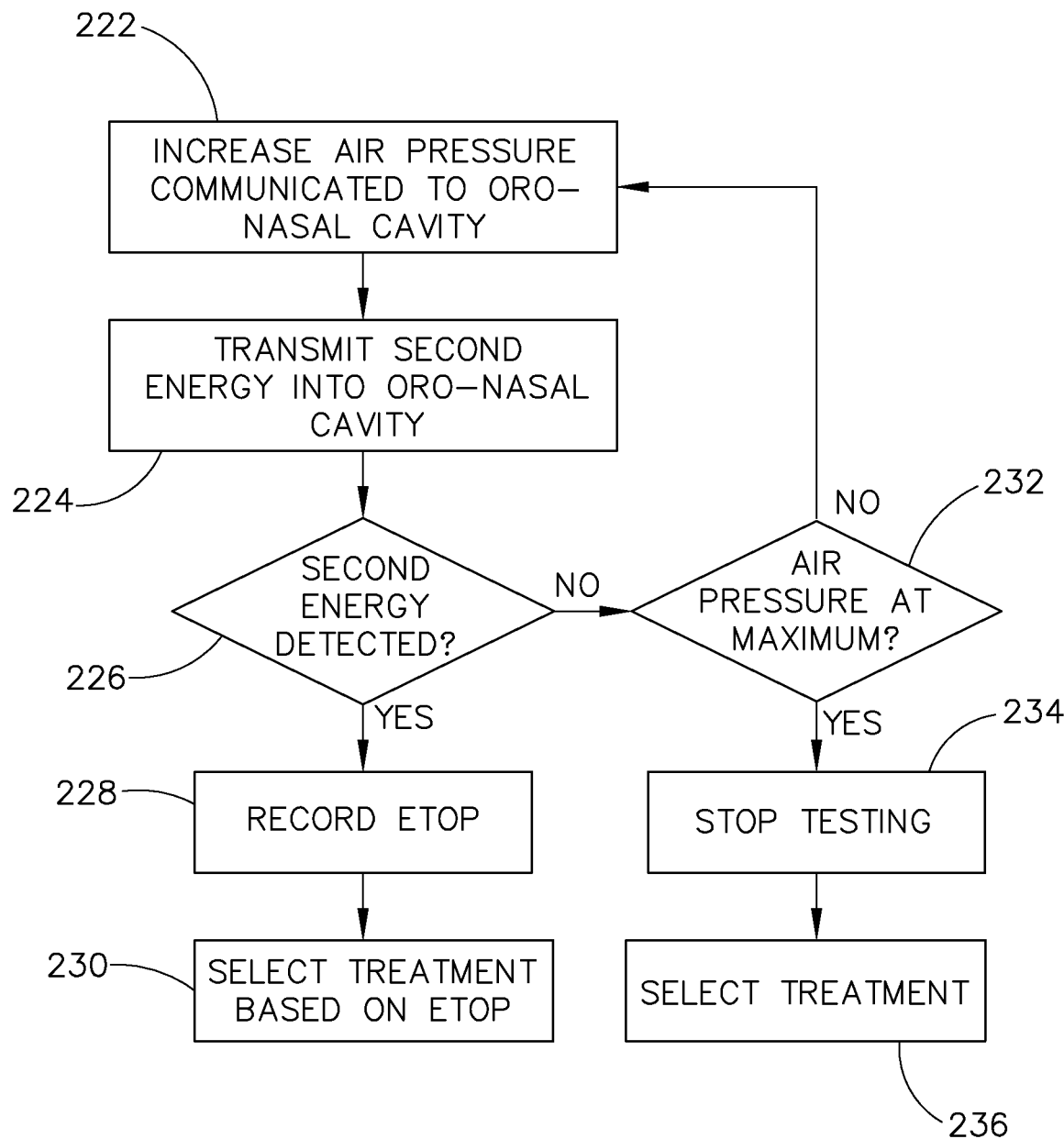
FIG. 8 depicts a flowchart detailing an exemplary method for determining a treatment for Eustachian tube.
Figure 10:
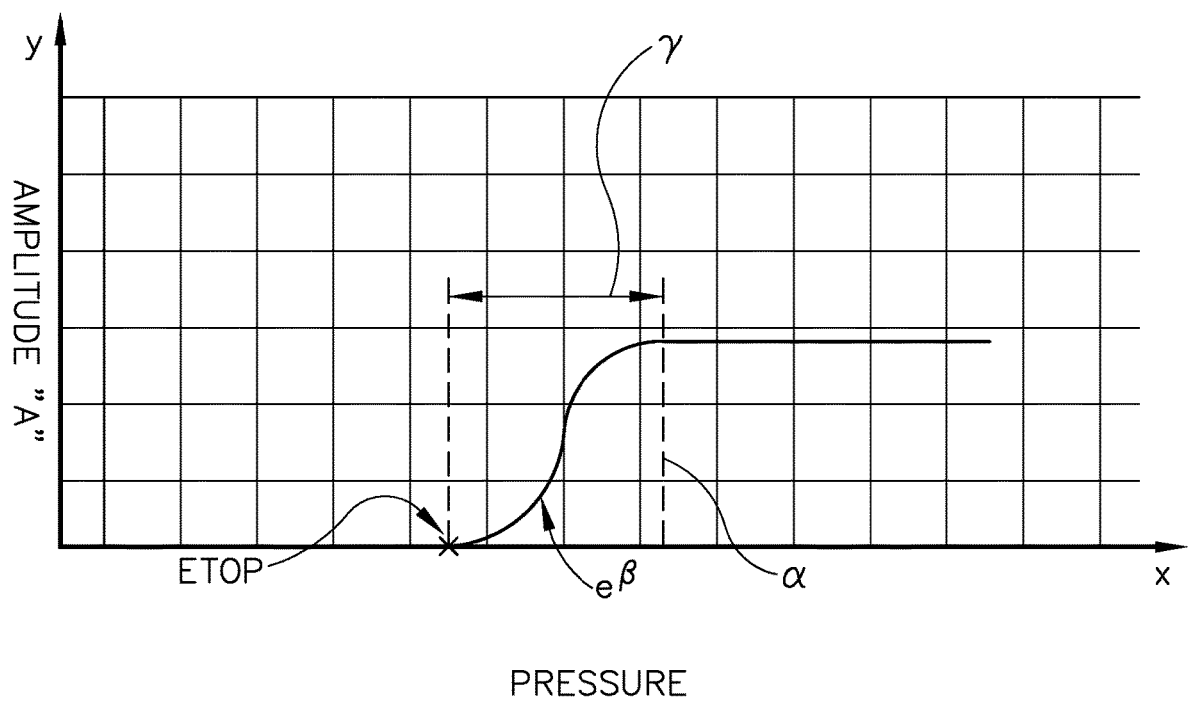
FIG. 10 depicts an exemplary plot of baseline pressure vs. amplitude of an energy input of the system of FIG. 4.

It is possible to perform the methods of FIGS. 7 and 8 during one or both of the passive or active states of the ET (26). As described herein, "active" refers to the behavior/state of the ET (26) during actions such as swallowing or the Valsalva maneuver, while passive refers to the behavior/state of the ET (26) while the ET (26) is resting (i.e., not being subjected to swallowing or the Valsava maneuver, for example). Measuring both active ETOP ($A_{ETOP}$) and passive ETOP ($P_{ETOP}$) is useful to establish benchmarks for parameters of a normally functioning ET (26) and of a diseased or abnormal ET (26) because where the muscular function of the ET (26) is intact, active ETOP should be greater than passive ETOP. Therefore, because ETOP levels can vary from patient to patient, it is useful to have this benchmark for determining whether the ET (26) may be diseased or abnormal without having to compare one patient's ETOP with other patients' ETOP data. Moreover, knowing such parameters provides objective benchmarks against which progression of therapy or treatment may be measured. Referring to FIG. 10, where $\alpha=P_{ETOP}$, $\beta=A_{ETOP}$, and $\gamma$=change between $P_{ETOP}$ and $A_{ETOP}$, ETOP, Amplitude A, $\alpha$, $e^\beta$, and $\gamma$ may all correlate with disease state in ET.

Once treatment is selected according to the teachings herein, the clinician may treat the ET (26) according to such methods disclosed in U.S. Patent Application Pub. No. 2010/0274188, entitled "Method and System for Treating Target Tissue Within the Eustachian Tube," published on Oct. 28, 2010, now abandoned, the disclosure of which is incorporated by reference herein; U.S. Patent Application No. 2013/0274715, entitled "Method and System for Eustachian Tube Dilation," published on Oct. 17, 2013, now abandoned, the disclosure of which is incorporated by reference herein; U.S. patent application Ser. No. 14/317,269, entitled "Vent Cap for a Eustachian Tube Dilation System," filed Jun. 27, 2014, issued as U.S. Pat. No. 10,350,396 on Jul. 16, 2019, the disclosure of which is incorporated by reference herein. Other methods of treatment include delivering drugs, ET dilatation, surgery, irrigation, ventilation, or any other therapeutic method or process for ear conditions, such as those disclosed herein or in the above referenced applications. Moreover, because the ETOP will be known by use of the methods described herein, certain therapies may be aerosolized, injected, or otherwise delivered or introduced in conjunction with the diagnostic methods described herein (e.g., the ETOP may be used to open the ET (26) for therapy), in order to enhance access to the middle ear for the therapeutic device being introduced.

While the testing method of the present example is discussed in the context of detecting the condition of the ET (26), it should be understood that the same method (and variations thereof) may be used to detect the condition of various other anatomical structures that are either within the oro-nasal cavity or in communication with the oro-nasal cavity. Various other suitable anatomical features that may be tested using the method described above (and variations of the method described above) will be apparent to those of ordinary skill in the art in view of the teachings herein.

III. Overview of Exemplary Eustachian Tube Dilation Catheter System

One example of a treatment that may be performed, in addition or as an alternative to those treatments described herein, includes accessing and dilating the ET (26) using a guide catheter (300) and a balloon dilation catheter (400), (see FIGS. 11A-14). An exemplary guide catheter (300) is shown in FIG. 11A. As shown, the guide catheter (300) includes an elongate tubular shaft (302) that has a proximal end (304), a distal end (306) and a lumen (308) therebetween. The guide catheter (300) may have any suitable length, diameter, angle of bend, and location of the bend along the length of the catheter (300), to facilitate accessing an ET opening, such as the pharyngeal ostium (28). In some examples, the guide catheter (300) may have a length between about 8 cm and about 20 cm, and more preferably between about 10 cm and about 15 cm and often about 11 cm.

FIG. 11B is a cross-sectional view of the guide catheter elongate tubular shaft (302). As can be seen, shaft (302) has an outer shaft tube (310), an inner shaft tube (312) and a lumen (308). The outer shaft tube (310) may be constructed of a stiff material such as stainless steel and the inner shaft tube (312) may be constructed of a more flexible material such as a polymeric material including but not limited to nylon and further including a PTFE liner. The lumen (308) has a diameter of between about 2 mm and about 3 mm preferably between about 2.5 mm and about 2.6 mm such that the balloon dilation catheter (400) of FIGS. 13A-14 can be easily inserted into the lumen (308) for dilation of the ET (26). The combination of guide catheter (300) and balloon catheter (400) may a compact system that is designed for a one-handed procedure. By compact it is intended that the length of the guide catheter shaft that is distal of the bend in the guide catheter (300) is between about 0.5 and about 2.0 cm, in some versions between about 1 and about 2 cm, and in some versions about 1 cm. The compactness may help reduce interference with other instruments, such as an endoscope that may be used to help in visualizing the positioning of the system as described below.

The distal portion (320) of guide catheter (300) is shown in an enlarged view in FIG. 8. The distal portion (320) of the guide catheter (300) may have a bend (322) with an angle between about 45 degrees and about 65 degrees, and more preferably between about 50 degrees and about 60 degrees and particularly about 55 degrees to facilitate access into the ET (26). The distal portion (320) of the guide catheter (300) is made of a transparent material such as a polymer including but not limited to nylon and PTFE such that balloon dilation catheter (400) is visible within the distal portion (320) and such that distal portion (320) is more flexible than the elongate shaft (302). The distal tip (324) of the distal portion (320) of the guide catheter (300) is made of PEBAX® (polyether block amide) such that it provides for atraumatic access to the ET (26), and may contain 20% barium sulfate or other similar radiopaque materials for visualizable access.

Referring again to FIG. 11A, the proximal portion (330) of guide catheter (300) includes a proximal hub (332) to aid in insertion of the balloon catheter (400) into the ET (26). The hub (332) has a larger diameter proximal end (334) and a smaller diameter middle section (336) to facilitate stabilization of the guide catheter (300) in the nose, rotation of the guide catheter (300) and insertion of the balloon catheter (400) as will be described in further detail below. The hub (332) is ergonomically designed for insertion, location and rotation with slight manipulations with one hand.

Balloon dilation catheter (400) is shown in FIG. 13A. The balloon dilation catheter (400) generally includes an elongate shaft (402) having a proximal end (414) and a distal end (418). The balloon dilation catheter (400) further includes a balloon (404) on the distal end (418) of the elongate shaft (402). The balloon (404) may be a polymer balloon (compliant, semi-compliant, or non-compliant). In one example, the balloon (404) may be a suitable non-compliant material such as, including but not limited to, polyethylene terepthalate (PET), PEBAX® (polyether block amide), nylon or the like. The balloon catheter (400) may include any size of balloon including but not limited to balloons of 2 mm to 8 mm in diameter or of between about 5 mm and 6 mm (when inflated) and 12 mm to 24 mm in working length (for example 2 mm×12 mm, 3.5 mm×12 mm, 5 mm×16 mm, 5 mm×24 mm, 6 mm×16 mm, 6 mm×20 mm, 6 mm×24 mm, 7 mm×16 mm and 7 mm×24 mm) The balloon dilation catheter (400) generally includes a proximally located connection (430) for inflating/activating the balloon (404).

The balloon (404) may be expanded to dilate the ET (26) after balloon (404) is placed in a desirable location in the ET (26). For example, the opening area of the ET (26) includes the pharyngeal ostium (28), and the dilation catheter (400) may be advanced to position the balloon (404) in the pharyngeal ostium (28). An endoscope (e.g., endoscope (460) of FIG. 15) may be used to assist in positioning the dilation catheter (400). The endoscope (460) may be advanced through the nasal passage to view the dilation catheter (400). A marker (408) on a shaft of the dilation catheter (400) can be viewed from the endoscope (460) to approximate a location of the balloon (404) relative to the opening of the ET (26) (e.g., pharyngeal ostium (28)) based on a distance of the marker (408) from a proximal end of the balloon (404). Accordingly, the dilation catheter (400) can be moved to place the marker in a desirable location before expansion of the balloon (404) in the ET (26).

The balloon dilation catheter (400) further includes an actuator (410). The actuator (410) has a proximal side (420) and a distal side (422). In the example shown in FIG. 13A, the actuator (410) is secured by an adhesive to the elongate shaft (402). The portion (440) of the elongate shaft (402) that is distal of the actuator (410) is sufficiently stiff to be guided through the nasal cavity and into the ET (26), and is constructed of stainless steel and preferably includes a stainless steel hypotube. The portion (438) of the elongate shaft (402) that is proximal of the actuator (410) and that portion (450) that is distal of portion (440) is more flexible than the portion (440) and is constructed of a polymeric material including but not limited to PEBAX® (polyether block amide). In this way, the proximal portion (438) of the elongate shaft (402) will not interfere with the endoscope described above as it is advanced through the nasal passage such that the dilation catheter (400) can be easily viewed. The actuator (410) allows for easy, ergonomic one-handed advancement of the dilation catheter (400) through the guide catheter (300) and into the ET (26). The actuator (410) may be used to advance or retract in alternative ways including but not limited to use of the thumb, the index finger, or a combination of fingers (i.e. the index and middle fingers) or the thumb and the index or middle finger.

The distal end (418) of the balloon catheter (400) further includes a tip (412) and a flexible shaft portion (450) that is constructed of a polymeric material including but not limited to PEBAX® (polyether block amide) that extends from the distal end of the elongate shaft (402) to the proximal end of the balloon (404). In the example shown in FIG. 13A, the tip (412) is a bulbous polymeric blueberry shaped tip that is atraumatic and is about 1.5 mm to 2 mm in length with an outer diameter of between about 2 mm and 3 mm. The smoothness and roundness of tip (412) facilitates advancement of the balloon catheter (400) by helping it glide smoothly through the ET (26). The tip further acts as a safety stop. The isthmus (29) of the ET (26), shown in FIG. 1, is approximately 1 mm in diameter. The tip diameter is larger than the outer diameter (433) of the elongate shaft (402) shown in cross-section in FIG. 13B such that the size of tip (412) will prevent the balloon catheter (400) from passing through the isthmus (29) into the middle ear (14).

The balloon (404) may be held in location while in an expanded state for an extended period of time (e.g. several seconds or minutes). The balloon catheter (400) may also deliver a substance to the ET (26), such as one or more of the therapeutic or diagnostic agents described herein. The balloon (404) may also carry an expandable stent for delivery into the ET (26) upon expansion of the balloon (404). The balloon dilation catheter (400) and the guide catheter (300) may be removed from the patient after the balloon (404) has been deflated/unexpanded. The ET (26) will resume functioning, normally opening and closing to equalize atmospheric pressure in the middle ear and protect the middle ear from unwanted pressure fluctuations and loud sounds.

IV. Overview of Exemplary Endoscope

Figure 15:
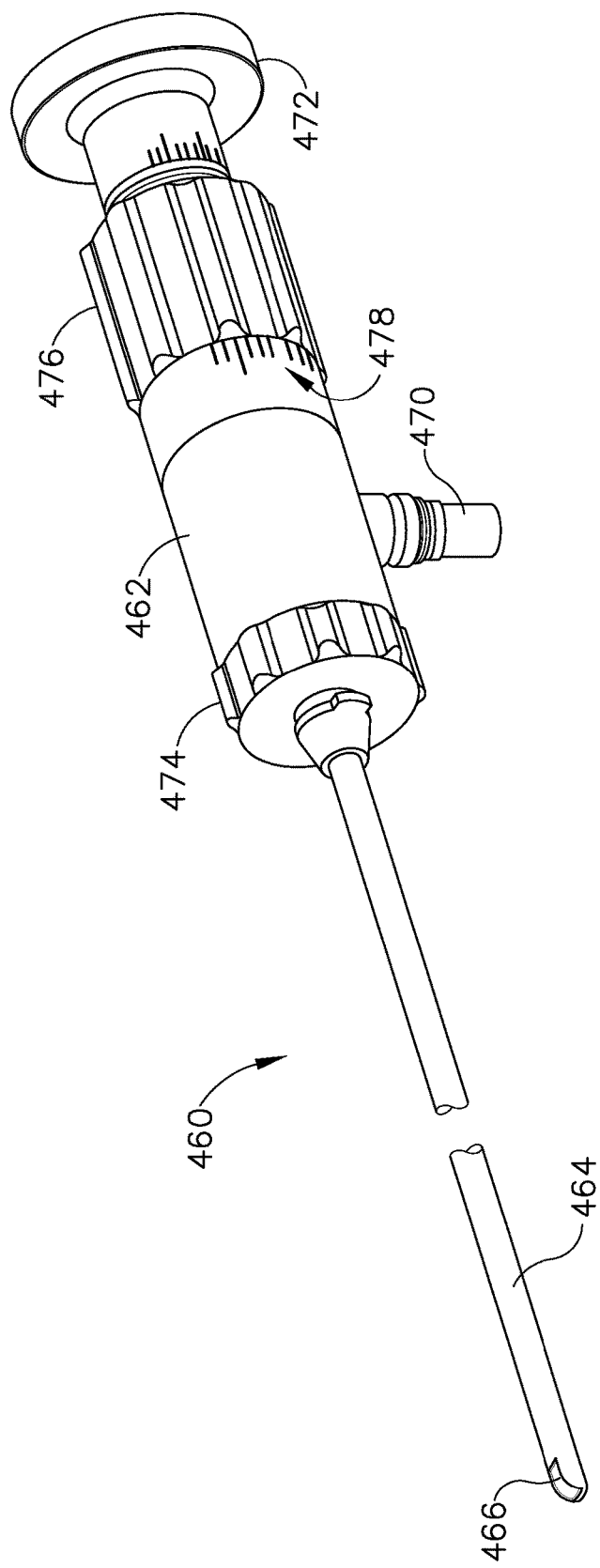
FIG. 15 depicts a perspective view of an exemplary endoscope suitable for use with the guide catheter of FIG. 11A and the balloon dilation catheter of FIG. 13A.
Figure 16:
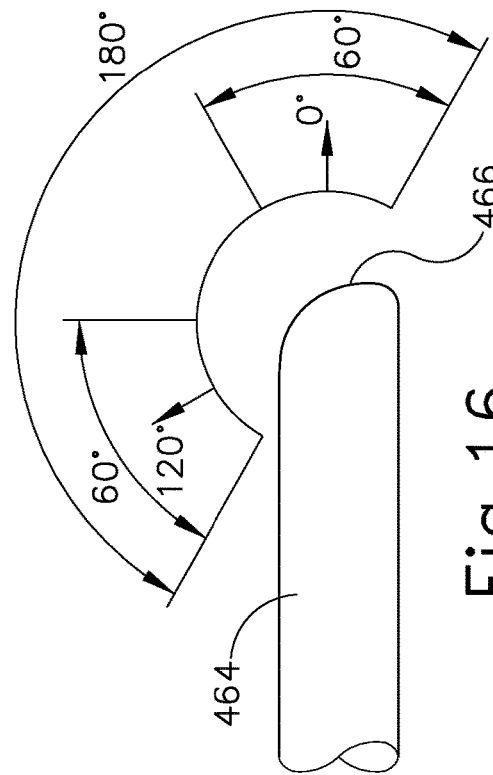
FIG. 16 depicts a side elevational view of the distal end of the endoscope of FIG. 15, showing an exemplary range of viewing angles.

Referring to FIGS. 15-16, an endoscope (460) may be used to provide visualization within an anatomical passageway (e.g., within the oro-nasal cavity, etc.) during the process using guide catheter (300) and/or balloon catheter (400) just described, or in another process, such as one involving system (100). As shown in FIGS. 15-16, endoscope (462) of the present example comprises a body (462) and a rigid shaft (464) extending distally from body (462). The distal end of shaft (464) includes a curved transparent window (466). A plurality of rod lenses and light transmitting fibers may extend along the length of shaft (464). A lens is positioned at the distal end of the rod lenses and a swing prism is positioned between the lens and window (466). The swing prism is pivotable about an axis that is transverse to the longitudinal axis of shaft (464). The swing prism defines a line of sight that pivots with the swing prism. The line of sight defines a viewing angle relative to the longitudinal axis of shaft (464). This line of sight may pivot from approximately 0 degrees to approximately 120 degrees, from approximately 10 degrees to approximately 90 degrees, or within any other suitable range. The swing prism and window (466) also provide a field of view spanning approximately 60 degrees (with the line of sight centered in the field of view). Thus, the field of view enables a viewing range spanning approximately 180 degrees, approximately 140 degrees, or any other range, based on the pivot range of the swing prism. Of course, all of these values are mere examples.

Body (462) of the present example includes a light post (470), an eyepiece (472), a rotation dial (474), and a pivot dial (476). Light post (470) is in communication with the light transmitting fibers in shaft (464) and is configured to couple with a source of light, to thereby illuminate the site in the patient distal to window (466). Eyepiece (472) is configured to provide visualization of the view captured through window (466) via the optics of endoscope (460). It should be understood that a visualization system (e.g., camera and display screen, etc.) may be coupled with eyepiece (472) to provide visualization of the view captured through window (466) via the optics of endoscope (460). Rotation dial (474) is configured to rotate shaft (464) relative to body (462) about the longitudinal axis of shaft (464). It should be understood that such rotation may be carried out even while the swing prism is pivoted such that the line of sight is non-parallel with the longitudinal axis of shaft (464). Pivot dial (476) is coupled with the swing prism and is thereby operable to pivot the swing prism about the transverse pivot axis. Indicia (478) on body (462) provide visual feedback indicating the viewing angle. Various suitable components and arrangements that may be used to couple rotation dial (474) with the swing prism will be apparent to those of ordinary skill in the art in view of the teachings herein. By way of example only, endoscope (460) may be configured in accordance with at least some of the teachings of U.S. Pub. No. 2010/0030031, now abandoned, the disclosure of which is incorporated by reference herein. In some versions, endoscope (460) is configured similar to the Acclarent Cyclops™ Multi-Angle Endoscope by Acclarent, Inc. of Menlo Park, Calif. Other suitable forms that endoscope (460) may take will be apparent to those of ordinary skill in the art in view of the teachings herein.

V. Exemplary Methods of Treating ET

Figure 17A:
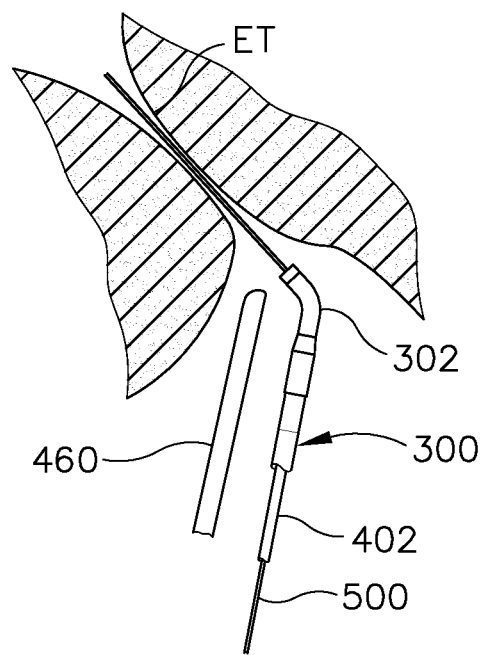
FIG. 17A depicts a schematic view of a guide catheter, a balloon catheter, and an endoscope being positioned in relation to a Eustachian tube of a patient, with a guidewire disposed in the Eustachian tube.
Figure 17B:
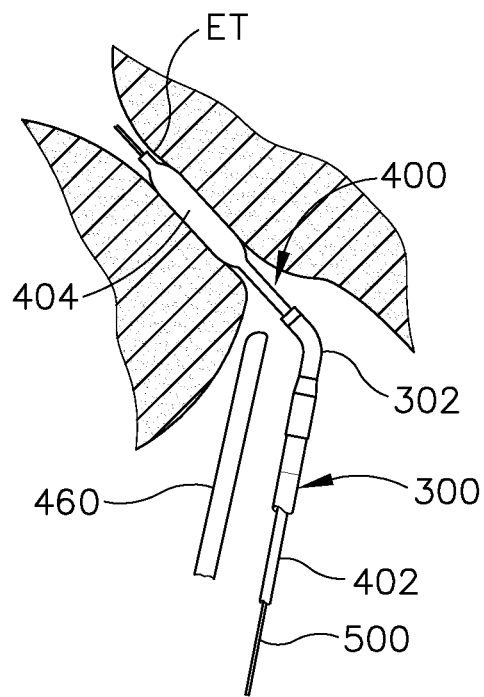
FIG. 17B depicts a schematic view of the guide catheter, balloon catheter, and endoscope of FIG. 17A, with a balloon of the balloon catheter being expanded to dilate the Eustachian tube.

FIGS. 17A-B show schematic versions of the guide catheter (300) and balloon catheter (400) being used to treat the ET (26) under visual guidance using endoscope (460). In use, the guide catheter (300) may be advanced into a nostril and through a nasal cavity to position a distal end of the catheter (300) at, in or near an opening into the ET (26). In one example, the guide catheter (300) may be passed through a nostril to the ET (26) on the ipsilateral (same side) of the head. In an alternative example, the guide catheter (300) may be passed through a nostril to the ET (26) on the contralateral (opposite side) of the head. A guiding element such as a guidewire (500) or illuminating fiber may be used to aid in accessing the ET (26). In some versions, guidewire (500) is omitted.

Referring to FIGS. 11A-14 and 17A-B, after the guide catheter (300) is in a desired position, balloon catheter (400) is advanced through the guide catheter (300) to position balloon (404) of the balloon catheter (400) within the ET (26). The physician/user may place the index and middle fingers on either side of the smaller diameter middle section (336) of the proximal hub (332) of the guide catheter (300). The physician/user will then place the thumb on the proximal side (420) of the actuator (410) or within both sides of the actuator (410) and will use the thumb to slide the balloon dilation catheter (400) through the guide catheter (300) to position the balloon (404) within the ET (26). Alternatively, the user may grasp the proximal hub (332) of the guide catheter (300) and use the index finger placed on the proximal side (420) of the actuator (410) or in between the distal side (422) and the proximal side (420) of the actuator (410) to advance the balloon catheter (400). The larger diameter tip (412) prevents the balloon catheter (400) from advancing too far into the middle ear (14). Further, the distal side (422) of the actuator (410) will bottom out against the proximal end (304) of the guide catheter (300), such that the balloon catheter (400) cannot advance any further. The actuator (410) prevents the balloon catheter (400) from reaching too far into the middle ear (14), which can cause damage to structures in the middle ear (14). Further the actuator (410) can be positioned at the appropriate distance along the elongate shaft (402) such that access to the ET (26) may be from the contralateral or the ipsilateral side.

In an alternative example, a balloon catheter (400) is advanced into a nostril of a patient without the use of a guide catheter. The balloon (404) of the balloon catheter (400) is placed within the ET (26). The physician/user will advance the balloon catheter (400) until the proximal side (420) of the actuator (410) is adjacent the patient's nostril. The distal side (422) of the actuator (410) will bottom out against the patient's nostril, such that the balloon catheter cannot advance any further. The actuator (410) prevents the catheter from reaching too far into the middle ear (14), which can cause damage to structures in the middle ear (14). Further the actuator (410) can be positioned at the appropriate distance along the elongate shaft (402) such that access to the ET (26) may be from the contralateral or the ipsilateral side.

Following placement of the balloon catheter (400) into the desired position any number of procedures may be carried out. The elongate shaft (402) contains adjacent dual lumen tubing (see FIG. 13B). By adjacent dual lumen tubing it is intended that the lumens are next to each other but are spaced apart, one from the other. The inflation lumen (432) is used for inflation of the balloon (404) with water, contrast medium, or saline through inflation port (430) to a pressure of between about 3 and 15 atmospheres, or of between about 6 and 12 atmospheres. The injection lumen (434) permits the optional injection of water, medicament, or even the introduction of a guidewire through the injection port (436) at the proximal end (416) of the proximal connector (406). In order to ensure that the inflation port (430) is used for balloon inflation only, the inflation port (430) and the injection port (436) may optionally have different type connectors. For example, the inflation port (430) may be a female connector whereas the injection port is a male connector or vice versa. Alternatively, the injection port may have a right-handed thread connector and the inflation port may have a left-handed thread connector or vice versa. It may be desirable to inject solutions containing contrast agents, pharmaceutically acceptable salt or dosage form of an antimicrobial agent (e.g. antibiotic, antiviral, anti-parasitic, antifungal, etc.), an anesthetic agent with or without a vasoconstriction agent (e.g. Xylocaine with or without epinephrine, Tetracaine with or without epinephrine, etc.), an analgesic agent, a corticosteroid or other anti-inflammatory (e.g. an NSAID), a decongestant (e.g. vasoconstrictor), a mucus thinning agent (e.g. an expectorant or mucolytic), a surfactant, an agent that prevents or modifies an allergic response (e.g. an antihistamine, cytokine inhibitor, leucotriene inhibitor, IgE inhibitor, immunomodulator), an allergen or another substance that causes secretion of mucous by tissues, hemostatic agents to stop bleeding, antiproliferative agents, cytotoxic agents (e.g. alcohol), biological agents such as protein molecules, stem cells, genes or gene therapy preparations, or the like.

Some nonlimiting examples of antimicrobial agents that may be used in this invention include acyclovir, amantadine, aminoglycosides (e.g., amikacin, gentamicin and tobramycin), amoxicillin, amoxicillinlclavulanate, amphotericin B, ampicillin, ampicillinlsulbactam, atovaquone, azithromycin, cefazolin, cefepime, cefotaxime, cefotetan, cefpodoxime, ceflazidime, ceflizoxime, ceftriaxone, cefuroxime, cefuroxime axetil, cephalexin, chloramphenicol, clotrimazole, ciprofloxacin, clarithromycin, clindamycin, dapsone, dicloxacillin, doxycycline, erythromycin, fluconazole, foscamet, ganciclovir, atifloxacin, imipenemlcilastatin, isoniazid, itraconazole, ketoconazole, metronidazole, nafcillin, nafcillin, nystatin, penicillin, penicillin G, pentamidine, piperacillinitazobactam, rifampin, quinupristindalfopristin, ticarcillinlclavulanate, trimethoprimlsulfamethoxazole, valacyclovir, vancomycin, mafenide, silver sulfadiazine, mupirocin (e.g., Bactroban, Glaxo SmithKline, Research Triangle Park, N.C.), nystatin, triamcinolonelnystatin, clotrimazolelbetamethasone, clotrimazole, ketoconazole, butoconazole, miconazole, tioconazole, detergent-like chemicals that disrupt or disable microbes (e.g., nonoxynol-9, octoxynol-9, benzalkonium chloride, menfegol, and N-docasanol); chemicals that block microbial attachment to target cells and/or inhibits entry of infectious pathogens (e.g., sulphated and sulphonated polymers such as PC-515 (carrageenan), Pro-2000, and Dextrin 2 Sulphate); antiretroviral agents (e.g., PMPA gel) that prevent retroviruses from replicating in the cells; genetically engineered or naturally occurring antibodies that combat pathogens such as anti-viral antibodies genetically engineered from plants known as "plantibodies;" agents which change the condition of the tissue to make it hostile to the pathogen (such as substances which alter mucosal pH (e.g., Buffer Gel and Acid form); non-pathogenic or "friendly" microbes that cause the production of hydrogen peroxide or other substances that kill or inhibit the growth of pathogenic microbes (e.g., *Lactobacillus*); antimicrobial proteins or peptides such as those described in U.S. Pat. No. 6,716,813 (Lin et al.,) which is expressly incorporated herein by reference or antimicrobial metals (e.g., colloidal silver).

Additionally or alternatively, in some applications where it is desired to treat or prevent inflammation the substances delivered in this invention may include various steroids or other anti-inflammatory agents (e.g., nonsteroidal anti-inflammatory agents or NSAIDS), analgesic agents or antipyretic agents. For example, corticosteroids that have previously administered by intranasal 10 administration may be used, such as beclomethasone (Vancenase® or Beconase), flunisolide (Nasalid®), fluticasone proprionate (Flonase®), triamcinolone acetonide (Nasacort®), budesonide (Rhinocort Aqua®), loterednol etabonate (Locort) and mometasone (Nasonex®). Other salt forms of the aforementioned corticosteroids may also be used. Also, other non-limiting examples of steroids that may be useable in the present invention include but are not limited to aclometasone, desonide, hydrocortisone, betamethasone, clocortolone, desoximetasone, fluocinolone, flurandrenolide, mometasone, prednicarbate; amcinonide, desoximetasone, diflorasone, fluocinolone, fluocinonide, halcinonide, clobetasol, augmented betamethasone, diflorasone, halobetasol, prednisone, dexarnethasone and methylprednisolone. Other anti-inflammatory, analgesic or antipyretic agents that may be used include the nonselective COX inhibitors (e.g., salicylic acid derivatives, aspirin, sodium salicylate, choline magnesium trisalicylate, salsalate, diflunisal, sulfasalazine and olsalazine; para-aminophenol derivatives such as acetaminophen; indole and indene acetic acids such as indomethacin and sulindac; heteroaryl acetic acids such as tolmetin, dicofenac and ketorolac; arylpropionic acids such as ibuprofen, naproxen, flurbiprofen, ketoprofen, fenoprofen and oxaprozin; anthranilic acids (fenamates) such as mefenamic acid and meloxicam; enolic acids such as the oxicams (piroxicam, meloxicam) and alkanones such as nabumetone) and Selective COX-2 Inhibitors (e.g., diaryl-substituted furanones such as rofecoxib; diaryl-substituted pyrazoles such as celecoxib; indole acetic acids such as etodolac and sulfonanilides such as mmesulide).

Additionally or alternatively, in some applications, such as those where it is desired to treat or prevent an allergic or immune response and/or cellular proliferation, the substances delivered in this invention may include a) various cytokine inhibitors such as humanized anti-cytokine antibodies, anti-cytokine receptor antibodies, recombinant (new cell resulting from genetic recombination) antagonists, or soluble receptors; b) various leucotriene modifiers such as zafirlukast, montelukast and zileuton; c) immunoglobulin E (IgE) inhibitors such as Omalizumab (an anti-IgE monoclonal antibody formerly called rhu Mab-E25) and secretory leukocyte protease inhibitor) and d) SYK Kinase inhibitors such as an agent designated as "R-112," manufactured by Rigel Pharmaceuticals, Inc, South San Francisco, Calif.

Additionally or alternatively, in some applications, such as those where it is desired to shrink mucosal tissue, cause decongestion, or effect hemostasis, the substances delivered in this invention may include various vasoconstrictors for decongestant and or hemostatic purposes including but not limited to pseudoephedrine, xylometazoline, oxymetazoline, phenylephrine, epinephrine, etc.

Additionally or alternatively, in some applications, such as those where it is desired to facilitate the flow of mucous, the substances delivered in this invention may include various mucolytics or other agents that modify the viscosity or consistency of mucous or mucoid secretions, including but not limited to acetylcysteine. In one particular example, the substance delivered by this invention comprises a combination of an anti-inflammatory agent (e.g. a steroid or an NSAID) and a mucolytic agent.

Additionally or alternatively, in some applications such as those where it is desired to prevent or deter histamine release, the substances delivered in this invention may include various mast cell stabilizers or drugs which prevent the release of histamine such as cromolyn (e.g., Nasal Chroma) and nedocromil.

Additionally or alternatively, in some applications such as those where it is desired to prevent or inhibit the effect of histamine, the substances delivered in this invention may include various antihistamines such as azelastine (e.g., Astylin) diphenhydramine, loratidine, etc.

Additionally or alternatively, in some examples such as those where it is desired to dissolve, degrade, cut, break or remodel bone or cartilage, the substances delivered in this invention may include substances that weaken or modify bone and/or cartilage to facilitate other procedures of this invention wherein bone or cartilage is remodeled, reshaped, broken or removed. One example of such an agent would be a calcium chelator such as EDTA that could be injected or delivered in a substance delivery implant next to a region of bone that is to be remodeled or modified. Another example would be a preparation consisting of or containing bone degrading cells such as osteoclasts. Other examples would include various enzymes of material that may soften or break down components of bone or cartilage such as collagenase (CGN), trypsin, trypsinlLEDTA, hyaluronidase, and tosyllysylchloromethane (TLCM).

Additionally or alternatively, in some applications such as those wherein it is desired to treat a tumor or cancerous lesion, the substances delivered in this invention may include antitumor agents (e.g., cancer chemotherapeutic agents, biological response modifiers, vascularization inhibitors, hormone receptor blockers, cryotherapeutic agents or other agents that destroy or inhibit neoplasia or tumorigenesis) such as; alkylating agents or other agents which directly kill cancer cells by attacking their DNA (e.g., cyclophosphamide, isophosphamide), nitrosoureas or other agents which kill cancer cells by inhibiting changes necessary for cellular DNA repair (e.g., carmustine (BCNU) and lomustine (CCNU)), antimetabolites and other agents that block cancer cell growth by interfering with certain cell functions, usually DNA synthesis (e.g., 6 mercaptopurine and 5-fluorouracil (5FU), antitumor antibiotics and other compounds that act by binding or intercalating DNA and preventing RNA synthesis (e.g., doxorubicin, daunorubicin, epirubicin, idarubicin, mitomycin-C and bleomycin) plant (vinca) alkaloids and other antitumor agents derived from plants (e.g., vincristine and vinblastine), steroid hormones, hormone inhibitors, hormone receptor antagonists and other agents which affect the growth of hormone-responsive cancers (e.g., tamoxifen, herceptin, aromatase inhibitors such as aminoglutethamide and formestane, trriazole inhibitors such as letrozole and anastrazole, steroidal inhibitors such as exemestane), antiangiogenic proteins, small molecules, gene therapies and/or other agents that inhibit angiogenesis or vascularization of tumors (e.g., meth-I, meth-2, thalidomide), bevacizumab (Avastin), squalamine, endostatin, angiostatin, Angiozyme, AE-941 (Neovastat), CC-5013 (Revimid), medi-522 (Vitaxin), 2-methoxyestradiol (2ME2, Panzem), carboxyamidotriazole (CAI), combretastatin A4 prodrug (CA4P), SU6668, SU11248, BMS-275291, COL-3, EMD 121974, 1MC-IC11, 1M862, TNP-470, celecoxib (Celebrex), rofecoxib (Vioxx), interferon alpha, interleukin-12 (IL-12) or any of the compounds identified in Science Vol. 289, Pages 1197-1201 (Aug. 17, 2000) which is expressly incorporated herein by reference, biological response modifiers (e.g., interferon, *Bacillus* calmetteguerin (BCG), monoclonal antibodies, interluken 2, granulocyte colony stimulating factor (GCSF), etc.), PGDF receptor antagonists, herceptin, asparaginase, busulphan, carboplatin, cisplatin, carmustine, cchlorambucil, cytarabine, dacarbazine, etoposide, flucarbazine, fluorouracil, gemcitabine, hydroxyurea, ifosphamide, irinotecan, lomustine, melphalan, mercaptopurine, methotrexate, thioguanine, thiotepa, tomudex, topotecan, treosulfan, vinblastine, vincristine, mitoazitrone, oxaliplatin, procarbazine, streptocin, taxol, taxotere, analogslcongeners and derivatives of such compounds as well as other antitumor agents not listed here.

Additionally or alternatively, in some applications such as those where it is desired to grow new cells or to modify existing cells, the substances delivered in this invention may include cells (mucosal cells, fibroblasts, stem cells or genetically engineered cells) as well as genes and gene delivery vehicles like plasmids, adenoviral vectors or naked DNA, mRNA, etc. injected with genes that code for anti-inflammatory substances, etc., and, as mentioned above, osteoclasts that modify or soften bone when so desired, cells that participate in or effect mucogenesis or ciliagenesis, etc.

In one example, a local anesthetic, such as Lidocaine is injected through the injection lumen (434) prior to dilation of the ET (26). The injection lumen (434) can be used for venting during dilation so that pressure in the middle ear (14) does not increase or decrease.

In some instances, an operator may wish to use system (100) to repeat the methods described above with reference to FIGS. 7-8 after using balloon catheter (400) to dilate the ET (26). This testing may be done to determine whether the dilation procedure was successful. In the event that the testing reveals that the dilation procedure with balloon catheter (400) was unsuccessful, the dilation procedure may be repeated; and the ET (26) may then again be tested to determine of the second dilation procedure was successful. These dilation and testing procedures may be repeated as many times as desired until the testing reveals that the ET (26) has been suitably dilated; until the testing reveals that a different kind of treatment is warranted; or until the operator otherwise decides on an alternative method of proceeding.

Figure 18:
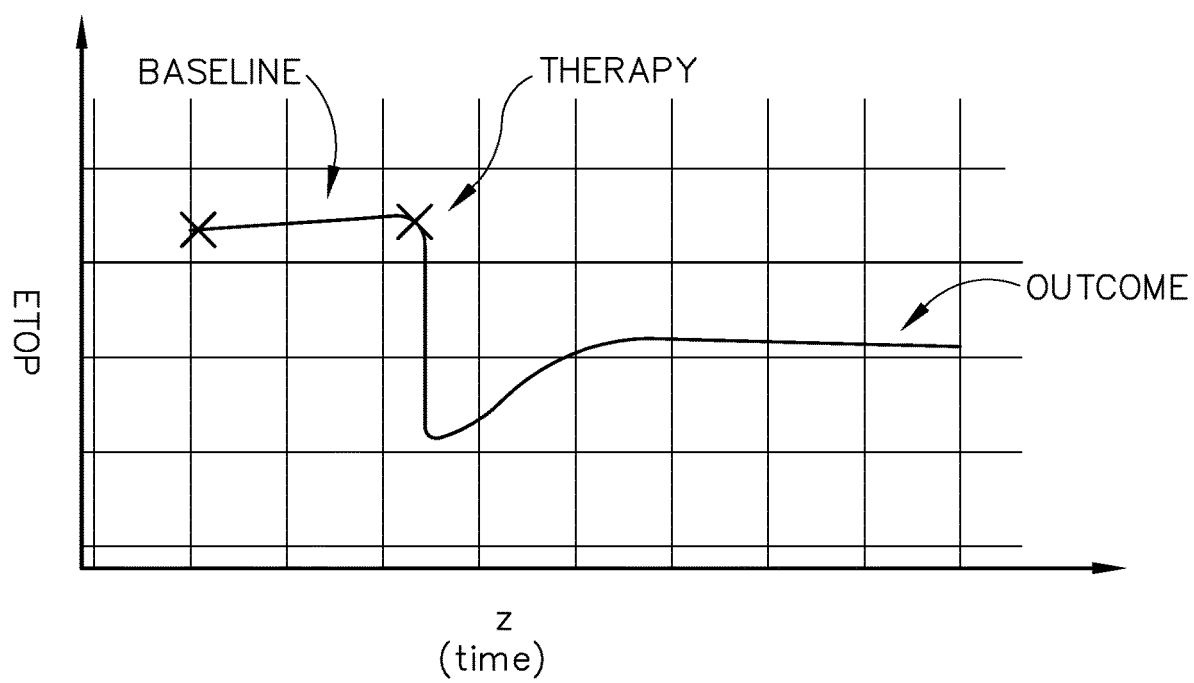
FIG. 18 depicts an exemplary plot of Eustachian tube opening pressure (ETOP) versus time.

In one example, the effectiveness of treatment may be measured by comparing the ETOP after treatment with the ETOP before treatment. Referring to FIG. 18, the initial ETOP as measured during, for example, the method according to FIG. 8, may be used as a baseline ETOP against which to compare the post-treatment ETOP. The post-treatment ETOP may be measured immediately after therapy or after a certain period of time that is sufficient for one of the treatments described herein to be effective in treating the ET (26) or other structures. The post-treatment ETOP may be measured in the same manner as shown and described with respect to FIG. 8. Additionally, the post-treatment ETOP may or may not be measured after a certain period of time to determine the overall outcome of therapy, again in the same manner as shown and described with respect to FIG. 8. Processor (116) may be configured to store the baseline ETOP of the patient such that the clinician may compare it to the treatment ETOP and outcome ETOP. Moreover, processor (116) may be configured to store and calculate trends in data regarding ETOP outcomes, for example, that result from particular therapies. Moreover, processor (116) may be able to communicate a particular outcome with a central system or database that includes outcomes associated with particular therapies. In some versions, the trends and other data stored by system (100) via processor (116) may be used to assist in selecting treatments based on ETOP values (block 230). Other suitable ways in which data may be processed by system (100) will be apparent to those of ordinary skill in the art in view of the teachings herein. Similarly, various suitable treatments that may be provided in response to data obtained using system (100) will be apparent to those of ordinary skill in the art in view of the teachings herein.

While the method described above with reference to FIGS. 7-8 relies on the communication of pressurized air in order to attempt opening the ET (26) (block 212, block 222), it should be understood that other methods may be used at any such stages of the process. For instance, the operator may proceed directly with insertion and expansion of a balloon catheter (400) in the ET (26) at any such stages in the process (e.g., at block 212 and/or at block 222).

VI. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A method for detecting characteristics of a Eustachian tube of a patient, comprising: (a) communicating pressurized air into an oro-nasal cavity of the patient; (b) directing an energy signal into the oro-nasal cavity; (c) detecting an absence or presence of the energy signal in the oro-nasal cavity with a sensor; and (d) determining at least one characteristic of the Eustachian tube based on an extent to which the energy signal is detected by the sensor.

Example 2

The method of Example 1, wherein directing an energy signal into the oro-nasal cavity further comprises directing the energy signal into the oro-nasal cavity at one end of the Eustachian tube, wherein detecting the energy signal in the oro-nasal cavity further comprises detecting the energy signal in the oro-nasal cavity at another end of the Eustachian tube.

Example 3

The method of any one or more of Examples 1 through 2, wherein the method further comprises positioning the sensor within or adjacent to the oro-nasal cavity.

Example 4

The method of Example 3, wherein the sensor further comprises an earpiece, wherein the method further comprises placing at least a portion of the earpiece within an ear canal of the patient.

Example 5

The method of any one or more of Examples 1 through 4, further comprising placing a facemask over the patient's mouth and nose, and wherein communicating pressurized air into the oro-nasal cavity further comprises communicating pressurized air into at least one of the nose or the mouth of the patient via the facemask.

Example 6

The method of Example 5, wherein directing an energy signal into the oro-nasal cavity further comprises directing the energy signal into the oro-nasal cavity via the facemask.

Example 7

The method of any one or more of Examples 1 through 6, wherein determining at least one characteristic of the Eustachian tube further comprises determining whether the Eustachian tube is open or closed, wherein when the sensor detects the energy signal, the Eustachian tube is open, wherein when the sensor does not detect the energy signal, the Eustachian tube is closed.

Example 8

The method of Example 7, further comprising recording and/or storing an overall pressure level in the oro-nasal cavity when sensor detects the energy signal.

Example 9

The method of Example 8, further comprising: (a) comparing the overall pressure level to a predetermined pressure level; and (b) determining whether the Eustachian tube is normal, abnormal, or patulous based on the comparison.

Example 10

The method of any one or more of Examples 7 through 9, wherein when the sensor does not detect the energy signal, the method further comprises increasing the overall pressure level into the oro-nasal cavity until the sensor senses the energy signal.

Example 11

The method of any one or more of Examples 1 through 10, further comprising selecting a treatment based on the at least one characteristic of the Eustachian tube.

Example 12

The method of Example 11, wherein the treatment comprises inserting a balloon dilation catheter into the Eustachian tube and dilating at least a portion of the Eustachian tube with a dilator of the balloon dilation catheter.

Example 13

The method of any one or more of Examples 1 through 12, wherein at least some of the steps are performed when the patient is swallowing or performing the Valsalva maneuver.

Example 14

The method of any one or more of Examples 1 through 13, further comprising varying a pressure level of the pressurized air.

Example 15

The method of any one or more of Examples 1 through 14, further comprising measuring a pressure level within the oro-nasal cavity associated with respiration.

Example 16

A system for detecting characteristics of the oro-nasal cavity, comprising: (a) an input device configured to emit pressurized air; (b) an energy emitter, wherein the energy emitter is configured to direct at least one type of energy signal into an oro-nasal cavity of the patient; (c) a sensor configured to be placed relative to the oro-nasal cavity in order to detect the at least one type of energy signal being emitted into the oro-nasal cavity of the patient; and (d) a facemask configured to fit over the patient's nose and mouth, wherein the facemask configured to be in fluid communication with the input device to thereby communicate pressurized air into the oro-nasal cavity of the patient.

Example 17

The system of Example 16, wherein the sensor further comprises an earpiece.

Example 18

The system of any one or more of Examples 16 through 17, wherein the energy emitter is configured to direct the at least one type of energy signal into the nose and/or mouth of the patient.

Example 19

The system of any one or more of Examples 16 through 18, further comprising a processor configured to control the input device and the energy emitter.

Example 20

A method for determining an opening pressure of a Eustachian tube, comprising: (a) communicating pressurized air into an oro-nasal cavity of the patient; (b) directing an energy signal into one end of the Eustachian tube; (c) detecting an absence or presence of the energy signal with a sensor at another end of the Eustachian tube; and (d) determining whether the Eustachian tube is open or closed based on the extent to which the energy signal is detected by the sensor.

VII. Miscellaneous

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometric s, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

I claim:

1. A method for detecting characteristics of a Eustachian tube of a patient, comprising:
    (a) directing energy from an energy emitter into an oro-nasal cavity at a first end of the Eustachian tube;
    (b) detecting an absence of the energy in the oro-nasal cavity with a sensor at a second end of the Eustachian tube;
    (c) directing pressurized air from a pressurized air source into the oro-nasal cavity of the patient after directing the energy into the oro-nasal cavity;
    (d) directing the energy from the energy emitter into the oro-nasal cavity while the patient refrains from breathing after directing the energy into the oro-nasal cavity, wherein the energy is different from the pressurized air;
    (e) detecting an absence or presence of the energy in the oro-nasal cavity with the sensor; and
    (f) determining at least one characteristic of the Eustachian tube based on an extent to which the energy is detected by the sensor.

2. The method of claim 1, wherein the method further comprises positioning the sensor within or adjacent to the oro-nasal cavity.

3. The method of claim 2, wherein the sensor further comprises an earpiece, wherein the method further comprises placing at least a portion of the earpiece within an ear canal of the patient.

4. The method of claim 1, further comprising placing a facemask over the patient's mouth and nose, and wherein communicating pressurized air into the oro-nasal cavity further comprises communicating pressurized air into at least one of the nose or the mouth of the patient via the facemask.

5. The method of claim 4, wherein directing the energy into the oro-nasal cavity further comprises directing the energy into the oro-nasal cavity via the facemask.

6. The method of claim 1, wherein determining at least one characteristic of the Eustachian tube further comprises determining whether the Eustachian tube is open or closed, wherein when the sensor detects the energy, the Eustachian tube is open, wherein when the sensor does not detect the energy, the Eustachian tube is closed.

7. The method of claim 6, further comprising recording and/or storing an overall pressure level in the oro-nasal cavity when sensor detects the energy.

8. The method of claim 7, further comprising:
   (a) comparing the overall pressure level to a predetermined pressure level; and
   (b) determining whether the Eustachian tube is normal, abnormal, or patulous based on the comparison.

9. The method of claim 6, wherein when the sensor does not detect the energy, the method further comprises increasing the overall pressure level into the oro-nasal cavity until the sensor senses the energy.

10. The method of claim 1, further comprising selecting a treatment based on the at least one characteristic of the Eustachian tube.

11. The method of claim 10, wherein the treatment comprises inserting a balloon dilation catheter into the Eustachian tube and dilating at least a portion of the Eustachian tube with a dilator of the balloon dilation catheter.

12. The method of claim 1, wherein at least some of the steps are performed when the patient is swallowing or performing the Valsalva maneuver.

13. The method of claim 1, further comprising measuring a pressure level within the oro-nasal cavity associated with respiration.

14. A method for determining an opening pressure of a Eustachian tube, comprising:
   (a) directing pressurized air at a first air pressure from a pressurized air source into an oro-nasal cavity of the patient while the patient refrains from breathing, while simultaneously directing energy from an energy emitter into one end of the Eustachian tube while the patient refrains from breathing, wherein the energy is different from the pressurized air;
   (b) detecting an absence of the energy with a sensor at another end of the Eustachian tube;
   (c) directing pressurized air at a second air pressure from the pressurized air source into the oro-nasal cavity of the patient while the patient refrains from breathing, while simultaneously directing the energy from the energy emitter into the one end of the Eustachian tube while the patient refrains from breathing;
   (d) detecting an absence or presence of the energy with the sensor at another end of the Eustachian tube; and
   (e) determining whether the Eustachian tube is open or closed based on the extent to which the energy is detected by the sensor.

15. The method of claim 14, wherein at least some of the steps are performed when the patient is performing the Valsalva maneuver.

16. A method for detecting characteristics of a Eustachian tube of a patient, comprising:
   (a) placing a facemask over the patient's mouth and nose, wherein the facemask is configured to prevent the ingress or egress of sound so as to prevent the interference of outside sound;
   (b) directing pressurized air at a first air pressure from a pressurized air source into an oro-nasal cavity of the patient via the facemask;
   (c) directing energy, different from the pressurized air, into the oro-nasal cavity via the facemask;
   (d) detecting an absence of the energy in the oro-nasal cavity with a sensor;
   (e) directing pressurized air at a second air pressure greater than the first air pressure from the pressurized air source into the oro-nasal cavity of the patient via the facemask;
   (f) directing the energy, different from the pressurized air, into the oro-nasal cavity via the facemask;
   (g) detecting an absence of the energy in the oro-nasal cavity with the sensor;
   (h) repeating steps (e), (f), and (g) until a maximum allowable air pressure is reached, wherein the maximum allowable pressure is selected to prevent injury to the patient; and
   (i) selecting a treatment based on the absence of the energy in the oro-nasal cavity.

17. The method of claim 16, wherein steps (e) and (f) are performed simultaneously.

18. The method of claim 16, wherein selecting the treatment further comprises automatically suggesting a treatment based on the testing being stopped due to the maximum air pressure being reached.

19. The method of claim 1, wherein directing the energy further comprises directing the energy into the oro-nasal cavity at the first end of the Eustachian tube, and detecting the absence or presence of the energy further comprises detecting the absence or presence of the energy in the oro-nasal cavity with the sensor at the second end of the Eustachian tube.

20. The method of claim 1, wherein the pressured air has a first air pressure, wherein the method further comprises directing pressurized air at a second air pressure greater than the first air pressure from the pressurized air source into the oro-nasal cavity of the patient.

* * * * *